United States Patent
Nuthi et al.

(10) Patent No.: US 11,120,904 B2
(45) Date of Patent: Sep. 14, 2021

(54) IMAGING MODALITY MAINTENANCE SMART DISPATCH SYSTEMS AND METHODS

(71) Applicant: General Electric Company, Schenectady, NY (US)

(72) Inventors: Sridhar Nuthi, Waukesha, WI (US); Deborah Babula, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 316 days.

(21) Appl. No.: 16/232,505

(22) Filed: Dec. 26, 2018

(65) Prior Publication Data
US 2020/0211699 A1 Jul. 2, 2020

(51) Int. Cl.
G16H 40/20 (2018.01)
G06F 21/35 (2013.01)
G16H 50/20 (2018.01)
G06F 11/00 (2006.01)

(52) U.S. Cl.
CPC .......... G16H 40/20 (2018.01); G06F 11/008 (2013.01); G06F 21/35 (2013.01); G16H 50/20 (2018.01)

(58) Field of Classification Search
CPC ...... G16H 40/20; G16H 50/20; G06F 11/008; G06F 21/35
USPC ........................................................ 705/2-3
See application file for complete search history.

(56) References Cited

U.S. PATENT DOCUMENTS

| | | | | |
|---|---|---|---|---|
| 6,381,557 B1 * | 4/2002 | Babula | ................ | G16H 40/40 702/183 |
| 6,882,271 B2 * | 4/2005 | Hendrickson | ....... | G06F 11/2247 340/286.07 |
| 8,121,856 B2 * | 2/2012 | Huster | ................ | G16H 40/40 705/2 |
| 8,489,408 B2 * | 7/2013 | Sawanaga | ............. | G06Q 10/06 705/2 |

(Continued)

FOREIGN PATENT DOCUMENTS

| | | | | |
|---|---|---|---|---|
| WO | WO-2018215666 A1 * | 11/2018 | ............. | H04L 67/34 |
| WO | WO-2019130079 A1 * | 7/2019 | ............. | A61B 34/35 |

OTHER PUBLICATIONS

Islam, et al., The Internet of Things For Health Care: A Comprehensive Survey, Jan. 1, 2015, IEEE Access, vol. 3, pp. 678-708 (Year: 2015).*

(Continued)

*Primary Examiner* — Joy Chng

(57) ABSTRACT

Methods, apparatus, systems and articles of manufacture are disclosed. An example apparatus includes a technician selector to: identify at least one of a skill level, tools list, or replacement part list to fix a problem based on an identified problem corresponding to a service request from an imaging device; and access resources from a database of resources available to service the imaging device; a multiplier to weight resources based on at least one of the skill level, possessed tools in comparison to the tools list, possessed replacement parts in comparison to the replacement part list, distance to service location, or availability; and an interface to transmit the service request using a wireless communication to a repair device of the highest weighed resource, the service request to be augmented to include a configuration for the repair device to facilitate addressing of the service request by the highest weighted resource.

20 Claims, 14 Drawing Sheets

(56) References Cited

U.S. PATENT DOCUMENTS

| | | |
|---|---|---|
| 2004/0139176 A1 | 7/2004 | Farrell et al. |
| 2006/0184410 A1 | 8/2006 | Ramamurthy et al. |
| 2009/0006476 A1* | 1/2009 | Andreasen ............. G07C 5/008 |
| 2014/0032172 A1* | 1/2014 | McCarthy .......... G05B 23/0227 |
| | | 702/183 |
| 2016/0300178 A1* | 10/2016 | Perry ............. G06Q 10/063116 |
| 2018/0315260 A1* | 11/2018 | Anthony ................ G06N 20/00 |

OTHER PUBLICATIONS

Yu et al., EdgeCNN: A Hybrid Architecture For Agile Learning of Healthcare Data From IoT Devices, Dec. 1, 2018, 2018 IEEE 24th International Conference on Parallel and Distributed Systems (ICPADS), pp. 852-859 (Year: 2018).*

* cited by examiner

IMAGING MODALITY MAINTENANCE SMART DISPATCH SYSTEMS AND METHODS

FIELD OF THE DISCLOSURE

This disclosure relates generally to imaging systems, and, more particularly, to image modality maintenance smart dispatch systems and methods.

BACKGROUND

Manufactures of large machines (e.g., imaging machines in health care, turbines in energy, and engines in transportation) deploys such large machines to users/customers for use in the field. Due to the complications of such machines, some manufactures provide repair and/or upkeep services with teams of technicians to service the machines during scheduled maintenance and/or when the machine is malfunctioning and/or down. When a user has a problem with a deployed machine, the user contacts the manufacturer (e.g., via call, email, etc.) describing the problem (e.g., providing symptoms) and a technician is sent to fix the machine. Additionally, the manufacture and/or customer can schedule maintenance calls at set durations of time to verify that the machine is working properly.

SUMMARY

Certain examples provide a computer readable medium comprising instructions which, when executed, cause a machine to provide an image modality maintenance smart dispatch. The example computer readable medium includes instructions that cause the machine to model a problem using an artificial intelligence model of an imaging device based on information obtained from a service request from the imaging device. The example computer readable medium further includes instructions that cause the machine to identify at least one of a skill level, tools list, or replacement part list to fix the problem based on the modeling using the artificial intelligence model. The example computer readable medium further includes instructions that cause the machine to access resources from a database of resources available to service the imaging device to identify a set of one or more available resources. The example computer readable medium further includes instructions that cause the machine to in response to the service request for the imaging device corresponding to an issue, determine whether the issue of the imaging device corresponds to a critical error. The example computer readable medium further includes instructions that cause the machine to when the issue of the imaging device corresponds to the critical error, filter out resources that are not available to service the imaging device within a threshold amount of time to reduce the set of one or more available resources. The example computer readable medium further includes instructions that cause the machine to weight resources in the set of one or more available resources based on at least one of the skill level, possessed tools in comparison to the tools list, possessed replacement parts in comparison to the replacement part list, distance to service location, or availability to identify a highest weighted resource. The example computer readable medium further includes instructions that cause the machine to transmit the service request using a wireless communication to a repair device associated with the highest weighed resource.

Certain examples provide an apparatus to provide an image modality maintenance smart dispatch. The example apparatus includes a technician selector to identify at least one of a skill level, tools list, or replacement part list to fix a problem based on an identified problem corresponding to a service request from an imaging device and access resources from a database of resources available to service the imaging device. The apparatus further includes a multiplier to weight resources based on at least one of the skill level, possessed tools in comparison to the tools list, possessed replacement parts in comparison to the replacement part list, distance to service location, or availability. The apparatus further includes an interface to transmit the service request using a wireless communication to a repair device of the highest weighed resource, the service request to be augmented to include a configuration for the repair device to facilitate addressing of the service request by the highest weighted resource Certain examples provide a method to provide an image modality maintenance smart dispatch. The example method includes identifying at least one of a skill level, tools list, or replacement part list to fix a problem of a machine based on a digital twin of the machine. The method further includes accessing resources from a database of resources available to service an imaging device. The method further includes determining whether the problem of the imaging device corresponds to a critical error. The method further includes when the problem of the imaging device does correspond to the critical error, removing resources who are not available to service the imaging device within a threshold amount of time. The method further includes weighting resources based on at least one of the skill level, possessed tools in comparison to the tools list, possessed replacement parts in comparison to the replacement part list, distance to service location, or availability to determine a highest weighted resource. The method further includes transmitting a service request corresponding to the imaging device to a repair device of the highest weighed resource using a wireless communication.

BRIEF DESCRIPTION OF THE DRAWINGS

The figures are not to scale. In general, the same reference numbers will be used throughout the drawing(s) and accompanying written description to refer to the same or like parts.

DETAILED DESCRIPTION

Figure 1A:
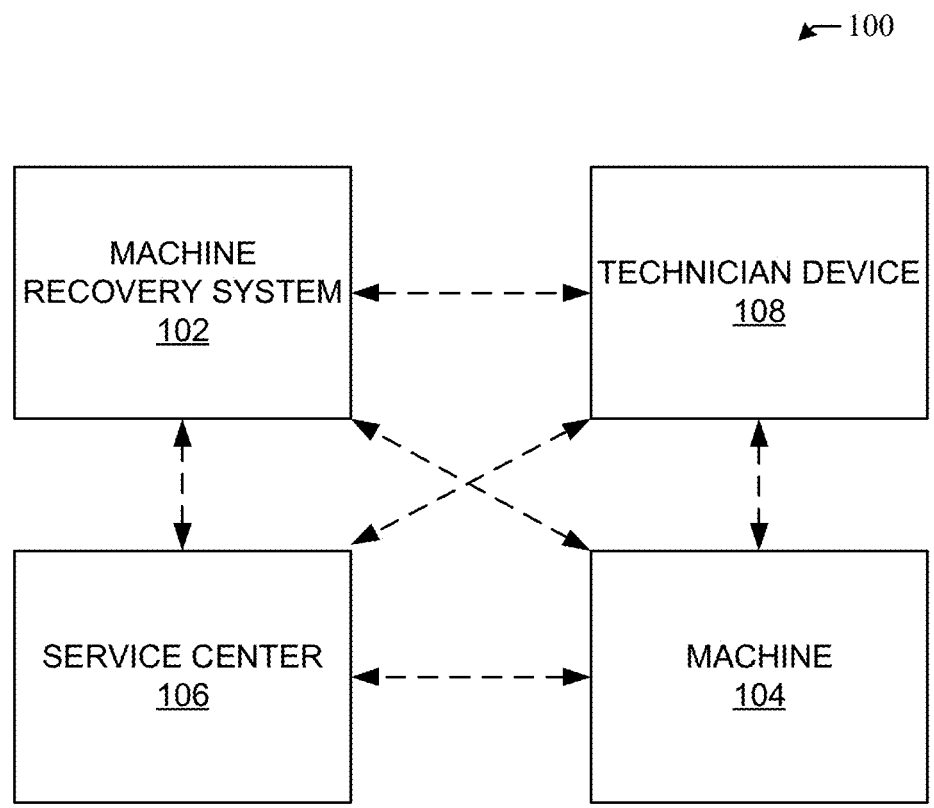
FIGS. 1A and/or 1B illustrate an example environment including a machine recovery system for servicing a universe of machines.

Fleet of machines, such as, but not limited to, imaging systems, turbines and engines are increasingly being deployed over large geographic regions. In the medical field, imaging systems including modalities such as magnetic resonance imaging (MRI), computed tomography (CT), nuclear imaging, and ultrasound are increasingly being deployed in hospitals, clinics, and medical research institutions for medical imaging of subjects. Engines deployed in locomotives or aircrafts, need to operate under varying environmental conditions. In power generation systems, wind turbines or water turbines are installed to harvest energy from natural resources. For facilities owning a machine belonging to a fleet of machines, it is desirable to maximize utilization of the machine with minimal downtime. However, system failures and breakdowns interrupt the workflow processes involving the machine and reduce its utilization.

Most manufacturers strive to provide effective periodic maintenance routines and responsive or on call repair services. Despite the refined capability of preventive maintenance programs, machines can sometimes develop problems which need out of turn diagnosis and repair. Usually, such problems are identified by a concerned authority at the facilities that manage the installed machine. The identified problems are submitted as service requests in one or more formats, such as, but not limited to, a textual description through a webform and a voice call through a helpline. As used herein, the term "service request" refers to a description of a problem, a fault, or issue associated with a machine, such as an imaging system. The problem, fault, or issue can be observed during routine maintenance check, or during usage of the machine, for example, by a technician or a user. The service request can be a description in text or audio message provided by the user via a user interface and can be automatically stored in a database.

Traditionally, servicing of a machine among the fleet of machines such as the imaging systems can require parts replacement or on-site visits by a field engineer to the site. Such on-site visits by field engineers can be expensive and time consuming for both customer and system manufacturer or repair facility, who typically arranges for such visits. Remote diagnosis and repair are often used to expedite system repair and obviate or minimize the need for such on-site visits. However, existing remote diagnosis and repair still entails the need to interrupt use of the imaging system and contact with the repair facility. Also, upon identification of a fault using remote diagnosis, manual intervention can be needed to submit a service request, initiate service request processing, and identify the requirement of an on-field visit.

Traditionally, an expert is required to manually scan huge amount of data pertaining to service requests, to make and/or recommend decisions about servicing options based on the service requests. Manual processing of service requests is inefficient and adversely effects the response time. Reducing manual overhead while processing servicing requests without compromising on accuracy and response times is desirable.

Examples disclosed herein provide a system for maintenance of machines that solves the problems of traditional techniques. Examples disclosed herein efficiently process service requests of machines belonging to a fleet of machines such as healthcare imaging systems, without or with minimal inherent work-flow delays. Examples disclosed herein include (A) a system to convert customer defined symptoms of a machine to actual problem/issues of the machine (e.g., smart symptom), (B) a system to develop a care package to provide to a resource (e.g., a technician, an automated program, etc.) that includes targeted and relevant information that can be useful in servicing the machine (e.g., smart care package), (C) a system to determine which technicians are best suited to service the request based on the customer demands (e.g., smart dispatch), (D) a system to identify a fleet of machine that correspound to the identified machine to use and/or develop an artificial intelligence model (e.g., a deep or machine learning model/digital twin) corresponding to the machine (e.g., smart find), and (E) a system to use technician feedback regarding the service request to update and fine tune the smart symptom, smart care package, smart dispatch, and smart find processes.

FIG. 1A is a schematic illustration of an environment 100 for servicing machines from a universe of machines. The environment 100 includes a machine recovery system 102, a machine 104, a service center 106, and a technician device 108. Although the environment 100 includes one machine 104, the environment is described in conjunction with a plurality of machines located in the same and/or difference locations.

The machine recovery system 102 of FIG. 1A performs various processes in response to a service request for the machine 104 and builds knowledge based on previous service request. Initially, the machine recovery system 102 receives a service request from the service center 106 and/or directly from the machine 104 when a problem occurs. For example, a user of the machine 104 can call and/or the machine 104 can otherwise communicate with the service center 106 to identify a problem with the machine and/or describe symptoms of the machine 104. In another example, the user can interface with a user interface of the machine 104 or a user interface of a computer to request servicing and/or identify symptoms of the machine 104. The machine recovery system 102 may, based on the request, perform a smart symptom process, a smart care package process, a smart dispatch process, a smart find process, and/or update data based on the servicing of requests from the machine 104 and other machines in a universe. The smart symptom process converts identified symptoms into machine issues. For example, a user of the machine 104 may not be able to determine the actual issue that the machine 104 is experiencing, but the user can identify symptoms that can be converted into one or more issues. The smart care package provides customized, relevant, actionable information to the technician device 108. The customized, relevant, actionable information corresponds to relevant manual/tutorial information, machine information, necessary tools, replacement parts, artificial intelligence model (e.g., deep or machine learning network model(s)/digital twin, etc.) information, predicted problems and/or solutions for the servicing, etc. The machine recovery system 102 generates the smart care package based on database information corresponding to previous servicing of the machine 104 and/or other machines. The smart dispatch process determines which resource(s) (e.g., technician(s), automated repair programs, etc.) to select to service the request based on various factors including, for example, the distance to the location, skill level of the technicians, availability of the technician, etc. The smart find system identifies a fleet of machines corresponding to the particular machine 104 based on the model, modality, make, and/or of contextual information of the machine 104. The fleet corresponds to a group of similar machines that can experience the same issues. Accordingly, the fleet corresponds to an artificial intelligence model/digital twin that can be used to test solutions virtually, during/prior to servicing. Additionally, information of the service request of the machine 104 can be added to the model/digital twin of the machine to update the model/digital twin for subsequent service requests from other machines in the fleet. Additionally, the machine recovery system 102 updates information in various databases (e.g., enterprise systems, problem solution database (PSDB), machine log database(s), and/or dynamic system health databases) to refine the smart symptom, smart care package, smart dispatch, and smart find processes for subsequent service requests of the machine 104 and other machines in the universe. The machine recovery system 102 is further described below in conjunction with FIG. 2.

The machine 104 of FIG. 1A is an imaging device or system that can require periodic servicing (e.g., based on a schedule) or aperiodic servicing (e.g., based on presence of an issue). Alternatively, the machine 104 can be any type of machine that can require periodic servicing or aperiodic servicing. For example, the machine 104 can be an imaging system (e.g., magnetic resonance imaging (MRI), computed tomography (CT), x-ray, nuclear imaging, or ultrasound, etc.), a turbine (e.g., wind turbine, water turbine, etc.), an engine (e.g., locomotive engine, aircraft engine, etc.), an information system (e.g., an imaging workstation, a picture archiving and communication system, a radiology information system, an image archive, an electronic medical record system, etc.), etc. When the machine 104 experiences an issue, a user can transmit a service request via a computer, via a phone (e.g., calling or texting), and/or the machine 104 itself can transmit a service request when an error or unexpected result occurs. The service request can be sent to the service center 106 and/or directly to the machine recovery system 102. In some examples, keywords from the service request can be extracted and processed to identify symptoms and/or issues with the machine 104. In some examples, the machine recovery system 102 can transmit distinguishing symptoms (e.g., directly or via the service center 106) to the user of the machine 104 to filter out possible issues.

The technician device 108 of FIG. 1A is a computing device (e.g., a laptop, a smart phone, a tablet, headset, etc.) that the technician and/or other resource can use to manage a schedule, receive service requests, look up information related to one or more machines to be serviced, identify error codes, symptoms, issues, and/or solutions, model the machine 104 (e.g., using an artificial intelligence model) to assist with repair, and/or interface with the imaging device to obtain additional data and/or confirm data. An implementation of example artificial intelligence models are further described below in conjunction with FIGS. 3 and/or 5. The machine recovery system 102 provides a custom care package including the relevant information that can be helpful for the technician or other resource to service the request. The care package can include one or more diagnostic and/or repair applications, knowledge base information, tool(s), script(s), routine(s), workflow(s), database(s), artificial intelligence model(s) (e.g., digital twin(s)) etc., to diagnose, remedy, and/or aid a resource (e.g., a technician, an automated service repair program, etc.) and/or the machine 104 in addressing an issue, for example.

When the technician device 108 of FIG. 1 has access to a digital twin, the technician device 108 (e.g., automatically) and/or a user of the technician device 108 can implement different service techniques (e.g., perform virtual actions, execute virtual instructions, etc.) on the digital twin to identify a potential problems that that can occur during the repair and/or identify an unexpected error that did occur during the repair. Additionally, after a resource fixes the machine 104, the resource can indicate that the service request is complete via the technician device 108. After such an indication, the machine recovery system 102 transmits a survey to the technician device 108 to obtain information corresponding to the service request and/or the care package. Additionally or alternatively, the technician device 108 can automatically output a survey to a technician once the service is complete and transmit the results to the machine recovery system 102. In some examples, the technician device 108 can interface (e.g., directly or via a wireless communication) with the machine 104 to gather data prior to, during, and/or after the machine 104 has been serviced. Such data can be transmitted to the machine recovery system 102 (e.g., separately and/or as part of a feedback response). The survey results (e.g., feedback) and/or obtained data can be used by an artificial intelligence model of the machine recovery system 102 to optimize future care packages, dispatches, machine finds, diagnoses (e.g., smart symptom processes), etc., to update databases to provide better recommendations for a subsequent service request and/or identify future problems for similar machines. Implementations of example technician devices 108 are further described below, in conjunction with FIGS. 4A-4C.

In some examples, the technician device 108 can be implemented as a repair device (e.g., for device-to-device repairs and/or to facilitate technician repair). For example, the technician device 108 can interface with the machine 104 (e.g., via a wired or wireless connection) to transmit instructions to the machine 104 to run diagnosis, gather information, and/or repair the device 108. For example, the technician device 108 can be a server or other network connected device that pushes instructions to the machine 104 (e.g., for remote repair). The instructions can cause the machine 104 to load a new version of code, apply a code patch, reboot the machine, and/or perform other processes to repair the machine 108.

Figure 1B:
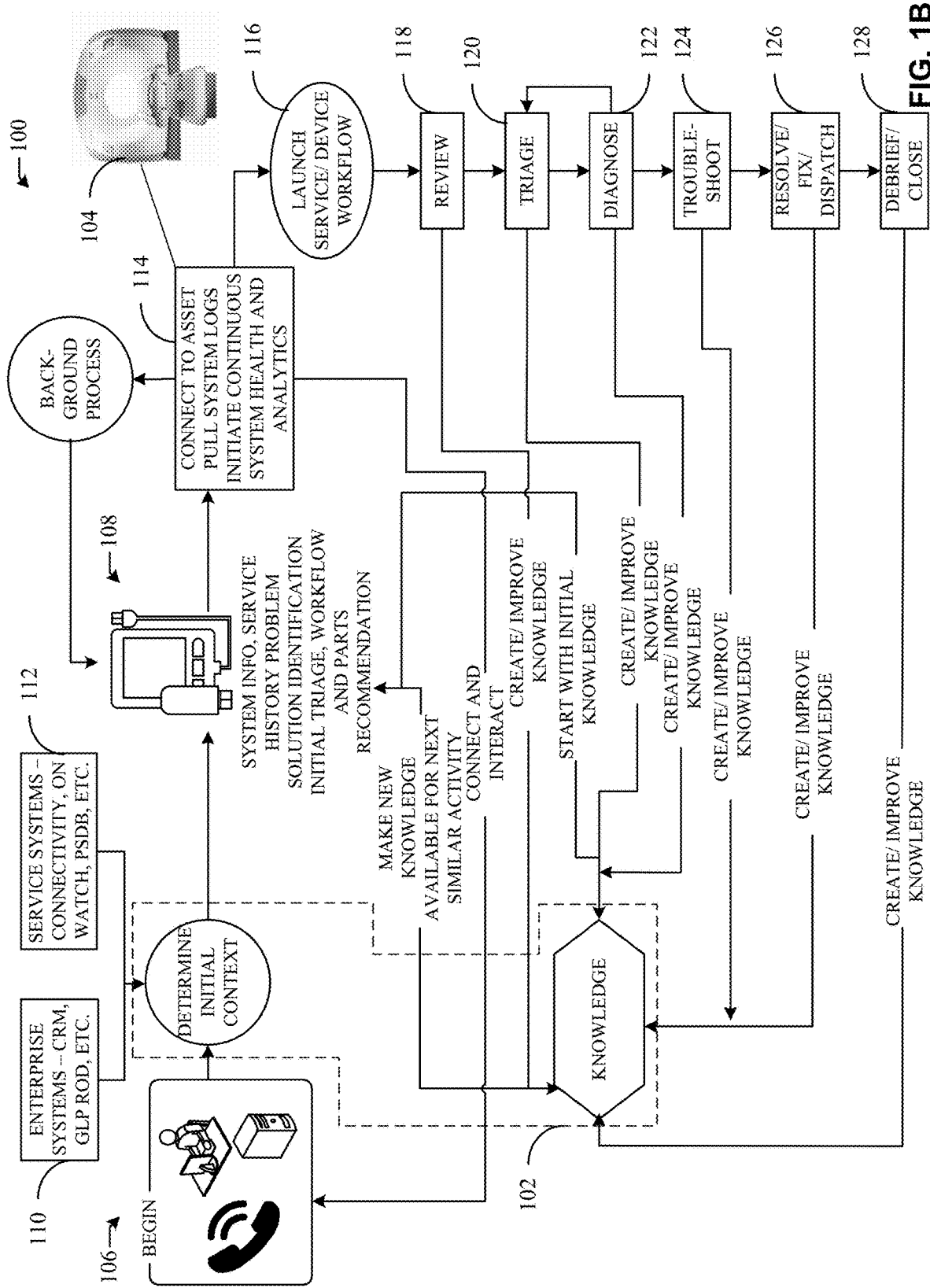

FIG. 1B illustrates information and/or process that may be performed in the example environment 100 of FIG. 1. FIG. 1B includes the machine recovery system 102, the machine 104, the service center 106, and the technician device 108 of FIG. 1A. FIG. 1B further includes example database systems 110, 112, example machine connection process 114, and an example service device workflow 116. The example service device workflow 116 includes example processes 118, 122, 124, 126, 128.

Initially, the service center 106 of FIG. 1B receives a service request from the machine 104 and/or a user of the machine 104 (e.g., via a phone, computing device, and/or the machine 104 itself). The service request can correspond to an problem that the machine 104 is having. In some examples, the service request is received directly by the machine recovery system 102. Once the service request is received, the service request is analyzed to determine what the potential solution(s) are. In some examples, the service center 102 utilizes database information from the enterprise system 110 and/or the service systems 112 to identify particular data related to the machine 104 (e.g., corresponding to the initial context). Additionally, the machine recovery system 102 develops potential solutions, digital models, and/or relevant information corresponding to the service request based on knowledge corresponding to prior service requests. The initial context and information from the prior knowledge can be transmitted the technician device 108 as part of a smart care package that is executed by the technician device to provide relevant customized data corresponding to solutions and/or information needed to fix the machine 104.

As described above, the technician device 108 obtains a care package corresponding to information that may aid the technician device 108 and/or a resource utilizing the technician device 108 in servicing the machine 104. In some examples, as shown in process 114, the technician device 108 may be connected to the machine 104 to obtain system logs, continuous system health, and/or other analytics corresponding to the machine 104. Such data may be obtained prior to, during, and/or after the servicing is complete. Such data (e.g., machine data or image device data) may be transmitted to the service center 106 and/or machine recovery system 102 to provide additional information that may be utilized to generate more accurate solution data, more accurate care package information, and/or better resource allocation (e.g., dispatches) for future service requests. Such data, along with survey data from the technician device 108 may be transmitted to the service center 106 as part of the device workflow 116.

As shown in the device workflow 116, each process 118, 120, 124, 126, 128 corresponds to data that may be used to create and/or improve the knowledge of the service center 106 for future service requests. For example, during the review process 118 information may be gathered corresponding to the machine 104 that may be used to triage and/or diagnose the problem of the machine 104. The service center 106 can use such data to draw connections between symptoms, error codes, issues, etc., of a machine and solutions, care packages, and/or other information needed to fix the machine 104. During the triage process 120, information can be obtained corresponding to the issues, symptoms, etc. that correspond to a critical error or a non-critical error, for example. Such information can be helpful for dispatching resources. During the diagnose process 122, information corresponding to digital twins, prior problem solution, implemented actions, etc., can be obtained by the service center 106 to optimize the diagnosis process for future service requests, for example. During the troubleshooting process 124, information corresponding to troubleshooting techniques can be obtained by the service center 106 to determine which techniques worked or did not work for future service requests, for example. During the resolve/fix/dispatch process 126, resolution information can be obtained by the service center 106 to update problem-solution information stored in a problem-solution database, for example. During the debrief/close process 128, survey result information can be obtained by the service center 106 from the technician device 108, for example. Such information may be used to update processes of the service center 106 for future service requests.

Figure 2:
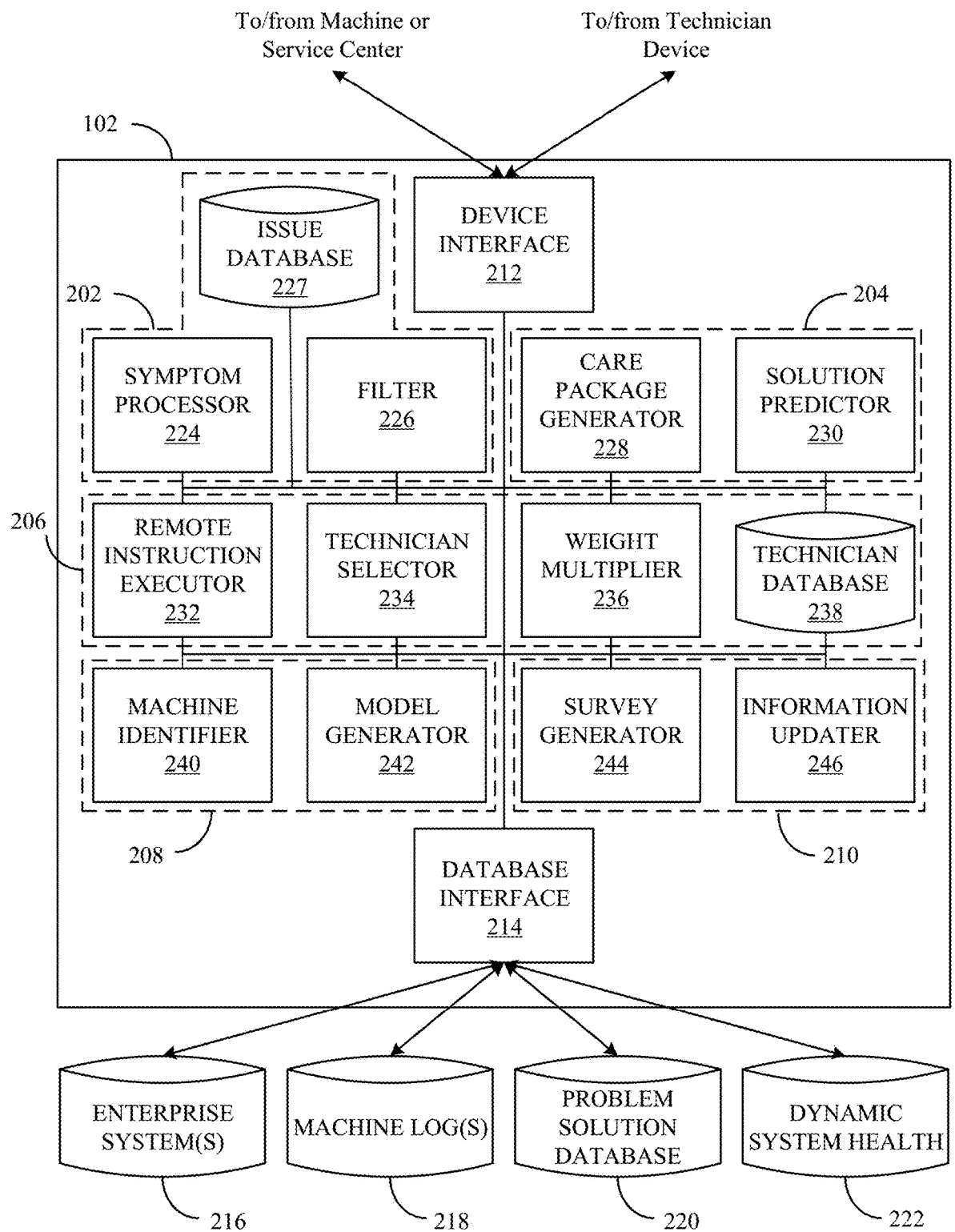
FIG. 2 is a block diagram of an example implementation of the machine recovery system of FIGS. 1A and/or 1B.

FIG. 2 is a block diagram of an example implementation of the machine recovery system 102 of FIGS. 1A and/or 1B. The machine recovery system 102 includes a smart symptom system 202, a smart care package system 204, a smart dispatch system 206, a smart find system 208, and a recovery updater system 210. The machine recovery system 102 further includes a device interface 212 to interface with deployed machines, the service center 106, and/or technician devices (e.g., the technician device 108) and a database interface 214 to interface with enterprise system(s) database 216, machine log database(s) 218, a problem solution database 220, and a dynamic system health database 222. The smart symptom system 202 includes a symptom processor 224 and a filter 226. The smart care package system 204 includes a care package generator 228 and a solution predictor 230. The smart dispatch system 206 includes a remote instruction executor 232, a technician selector 234 (e.g., a resource selector), and a weight multiplier 236. The smart find system 208 includes a machine identifier 240 and a model generator 242. The recovery updater system 210 includes a survey generator 244 and an information updater 246.

The smart symptom system 202 of FIG. 2 converts symptoms of a malfunctioning machine 104 into error codes and/or identified problems. For example, when a machine malfunctions, the operator of the machine 104 may not be able to identify the problem. Rather, the operator may only be able to identify symptoms that correspond to malfunctioning machine. Additionally or alternatively, the machine 104 can generate an error code corresponding to a particular part of the machine (e.g., which is stored in the machine log database 218), but not identify the problem itself. The smart symptom system 202 identifies the problems and/or error codes of the machine 104 based on the user-identified and/or machine-identified symptoms. The smart symptom system 202 includes the symptom processor 224 and the filter 226, as further described below.

The smart care package system 204 of FIG. 2 generates a smart care package for technicians and/or resources to aid in the repair of the machine. For example, once a problem is identified, the smart care package system 204 how to solve the problem, information that can be helpful in solving the problem, tools necessary to solve the problem, replacement parts that can be necessary to fix the problem, models that the technician can use to model possible fixes, etc. The care package system 204 generates the care package to provide the information to a device of the technician for use during/before a repair of the machine. The smart care package system 204 includes the care package generator 228 and the solution predictor 230, as further described below.

The smart dispatch system 206 of FIG. 2 determines how to dispatch resources (e.g., technician(s), automated repair programs, etc.) to fix a problem(s) of a machine. For example, the smart dispatch system 206 can look at the skill required to fix the machine, other machines in the clinical workflow that may also need to be serviced/checked, how critical the repair is, how many technicians or other resources should be available to service the request, the distance to the repair site, whether the solution can be performed remotely, etc. to select the optimal technician(s)/resource(s) to dispatch to service the machine. Although the smart dispatch system 206 can be described in conjunction with technicians as resources, other resources can be included in the smart dispatch process. For example, the smart dispatch system 206 can determine that an automated repair program can be utilized as a resource to implement instructions on the machine 104 to repair the machine using software patches, reboots, etc. A resource can include a computing device such as a laptop computer, tablet computer, smartphone, other handheld technician device, etc., that can connect to the machine 104 to facilitate diagnosis and/or repair of the machine 104 and/or other connected component(s), for example. The smart dispatch system 206 includes the remote instruction executor 232, the technician selector 234, and the weight multiplier 236, as further described below.

The smart find system 208 of FIG. 2 identifies machines based on contextual information (e.g., by comparing obtained information corresponding to the machine 104 to stored information in the enterprise system(s) database 216) and/or identifiers and determines whether the identified machine corresponds to a fleet of similar machines and/or machines deployed in similar environments. The smart find 208 can select and/or generate an artificial intelligence model (e.g., digital twin/model) based on parameters similar to the fleet of machines and use feedback to update the artificial intelligence model based on feedback information for more accurate and efficient diagnosis/dispatch/package generate for subsequent machine problems. Additionally, the smart find 208 tracks problems of the fleet to flag common problems for preemptive services (e.g., to identify upcoming problems and/or any other overall system statistical analysis). The smart find 208 includes the machine identifier 240 and the model generator 242, as further described below.

The updater system 210 of FIG. 2 updates information stored in the problem solution database 220, the dynamic system health database 222, layout and/or displayed information of the smart care package, and/or any other database based on determined error code(s) and/or feedback from a technician/resource once the service request is complete. Additionally, the updater system 120 can update various information used by processes disclosed herein using artificial intelligence models based on the technician/resource feedback. The machine recovery system 102 builds knowledge corresponding to previous machine servicing to be able to improve subsequent diagnoses, care packages, models/digital twins, dispatches, etc., based on the prior machine services using a neural network, for example. The updater system 210 includes the survey generator 244 and the information updater 246, as further described below.

The device interface 212 of FIG. 2 is a structural component that interfaces with the machine 104 and/or service center 106. For example, when there is a problem with one of the deployed machines, the machine 104 can automatically transmit information corresponding to the problem/error directly to the device interface via a wired or wireless network communication. Additionally or alternatively, the machine 104 can include an interface for a user to transmit problem and/or error information to a service center 106 and/or directly to the device interface 212. In some examples, a user of the machine 104 can determine that the machine 104 is not functioning properly and call the service center 106. In such an example, the service center 106 can include a user or processor that enters information regarding the machine 104 and/or symptoms of the machine 104 that is transmitted to the device interface 212. Additionally, the device interface 212 transmits care packages to selected technician devices (e.g., the technician device 108) to alert the technician/resource to the service request and provide the technician/resource with a smart care package corresponding to the information needed to service the machine. The device interface 212 also can transmit survey information to the technician device 108 to obtain feedback from the technician/resource after a service has been complete. The response is received via the device interface 212 from the technician device 108.

The database interface 214 of FIG. 2 is a structural component that interfaces with the databases 216, 218, 220, 222. In some examples, the database interface 214 obtains information from one or more of the databases 216, 218, 220, 222 via a wireless network communication. The machine recovery system 102 can perform a smart symptom, generate a smart care package, initiate a smart dispatch, and perform a smart find based on the information in the databases 216, 218, 220, 222. In some examples, the database interface 214 interfaces with the one or more databases 216, 218, 220, 222 to update the information in the database(s) 216, 218, 220, 222 based on identified error codes and/or feedback information from technicians and/or resources.

The enterprise system(s) database 216 of FIG. 2 is one or more databases and/or other data store/memory that store data corresponding to system identifiers, customer sites and layouts, contract warranties, asset locations, and/or other contextual information, etc. The information in the enterprise system(s) database 216 can initially be entered when a customer installs a machine and can be updated periodically or aperiodically based on updates to information of the machine. The enterprise system(s) database 216 can be located locally or can be located remotely. For example, a machine can include an enterprise system that communicates with the database interface 214 via a wireless network communication or the machine 104 can periodically or aperiodically transmit the enterprise system information to the enterprise system(s) database 216. The machine recovery system 102 uses such enterprise system information in conjunction with the smart find process, the smart symptom process, and/or the smart dispatch process. The enterprise system(s) database 216 can be one database for information of all deployed machines or the enterprise system(s) database 216 can be multiple databases corresponding to a customer, location, fleet, type, etc. The machine recovery system 102 uses such contextual information to determine symptom recognition from service history data and the description of a problem from a user. Additionally, the machine recovery system 102 can use the database information of a particular machine entered into the enterprise system database 216 for a particular customer site/geographical area (e.g., zip code, neighborhood, address, etc.) to determine how to best dispatch technicians/resources.

The machine log(s) 218 of FIG. 2 is one or more databases and/or other data store/memory that store data corresponding to machine logs of deployed machines, system health information, identifiers, error traces, utilization information and usage information, for example. The information in the machine log(s) 218 is provided by the deployed machines. The machine log(s) 218 can be located locally or can be located remotely. For example, the machine 104 can include a machine log at the machine 104 that communicates with the database interface 214 via a wireless network communication or the machine 104 can transmit periodically or aperiodically the machine log information to an offsite machine log(s) database. The machine log(s) 218 can be one database for information of all deployed machines or the machine log(s) 218 can be multiple databases corresponding to a customer, location, fleet, type, etc. The machine recovery system 102 uses such machine log information in conjunction with the smart find process, the smart care package process, and/or the smart symptom process. For example, the machine recovery system 102 can correlate information that users have historically used to describe a particular system issue with machine logs to develop an effective smart symptom to identify machine problems. Additionally, the machine recovery system 102 can identify system issues as idiosyncrasy issues or fleet level issues by looking at machine log information to identify correlations when an issue is identified.

The problem solution database 220 of FIG. 2 is a database and/or other data store, memory, etc., that stores data corresponding to prior problem and solutions correlations based on survey data from prior completed service requests. The problem solution database 220 can be located locally or can be located remotely. The problem solution database 220 can be one database for information of all deployed machines or the problem solution database 220 can be multiple databases corresponding to a customer, location, fleet, type, etc. The machine recovery system 102 uses such problem solution information in conjunction with the smart care package process, and/or the smart dispatch process. For example, the machine recovery system 102 can identify manual sections needed, replacement parts needed, and/or tools needed for a particular problem based on prior survey information to develop the smart care package. Additionally, the machine recovery system 102 can utilize problem solution information with the smart dispatch process whether problems can be categorized as a fleet problem or an idiosyncratic problem The dynamic system health database 222 of FIG. 2 is a database and/or other data store, memory, etc., that stores data corresponding to the health of deployed machines (e.g., corresponding to age of a machine in comparison to similar machines, problems identified, etc.). The dynamic system health database 222 can be located locally or can be located remotely. The dynamic system health database 222 can be one database for information of all deployed machines or the dynamic system health database 222 can be multiple databases corresponding to a customer, location, fleet, type, etc. The machine recovery system 102 uses such dynamic system health information in conjunction with the smart care package process and/or the smart symptom process. For example, the machine recovery system 102 can monitor the dynamic health of a machine as a service request is being reviewed to provide better capabilities of effecting smart logs and smart symptoms. By looking at the current health of the machine, a better decision can be made by the machine recovery system 102 on the actual problem and/or care package needed to solve the issue. For example, the system health of machines can be monitored by running a background daemon process that analyzes machining data in near real time and updating the system health in the dynamic system heath database 222 accordingly.

The symptom processor 224 of FIG. 2 receives identified symptoms from the machine 104 and/or service center 106 and uses known problem information (e.g., corresponding to data of the issue database 227) corresponding to the identified symptoms, machine logs, machine information, and dynamic health information to identify problems/issues and/or error codes that correspond to the identified symptoms based on problem solution information. For example, when a symptom is received from a user of a machine, the symptom processor 224 uses the health, machine information, and machine logs of the corresponding machine to identify error codes/issues that correspond to the identified symptoms. To decrease the set of error codes/issues, the symptom processor 224 can transmit a prompt for the user to identify whether or not a distinguishing symptom is present in the machine. A distinguishing symptom is a symptoms that is in one or more of the error codes/issues of the set and not in one or more error codes/issues of the set. For example, a symptom that is common to all error codes/issues in the set is not a distinguishing symptom. Additionally or alternatively, the symptom processor 224 can interface will the device directly via the device interface 212 to execute one or more processes to identify whether or not the distinguishing symptom is present in the machine.

Additionally or alternatively, the symptom processor 224 of FIG. 2 can interface with the machine 108 (e.g., directly using the device interface 212 and/or indirectly via the technician device 108, etc.) to obtain output data of the machine 104 (e.g., photos taken by the machine 104, etc.). In such examples, the symptom processor 224 can process an image obtained by the imaging device to identify an artifact (e.g., flaw) found on the image. The symptom processor 224 can uses identified flaws to identify a problem, a source of the problem, and/or additional symptoms. For example, the symptom processor 224 can, based on an identified flaw, determine that that there is not enough radiation, too much radiation, identify a failing detector, misalignment issues, etc. In some examples, the symptom processor 224 can compare the identified problem, source of problem, and/or symptoms associated with the flaw with previous problem-solution information (e.g., stored in the example problem solution database 220, etc.), to determine if the problem corresponds to a configuration and/or design flaw. In such examples, the symptom processor 224 may transmit an alert to the machine 108, a user of the machine 108 (e.g., via text, email, etc.), a system administrator, etc. identify the design flaw. Additionally, the machine identifier 240 may update fleet information and/or generate an alert to similar machines to identify the design flaw.

Once a response to the prompt to identify whether a distinguishing symptom is present in the machine, the filter 226 of FIG. 2 can filter out a set of issues from the issue database 227 into a subset based on whether or not distinguishing symptoms are present. For example, when a first half of the error codes/issues of a set corresponds to a distinguishing symptom and a second half of the error codes/issues of the set do not correspond to the distinguishing symptom, then the filter 226 filters out the first half of the set or the second half of the set to generate a subset based on whether a response to the prompt identifies whether or not the distinguishing feature is present in the machine.

The issue database 227 of FIG. 2 stores a listing of known issues. Additionally, the issue database 227 stores corresponding error codes and/or symptoms for the known issues. In some examples, when new issues are identified by a technician/resource, the technician/resource of the technician device 108 and/or the technician device 108 itself can enter information corresponding to the new issues via the technician device 108 and the issue database 227 update the stored data to include the new issues and corresponding error codes and/or symptoms. Additionally or alternatively, the machine 104 can transmit new error codes and/or a new combination of error codes that the issue database 227 can store as a new issue. Additionally or alternatively, a manager/system coordinator can add additional issues and corresponding error codes and/or symptoms into the issue database 227.

The care package generator 228 of FIG. 2 is a structural component that generates a customized care package for a service technician/resource with regards to a requesting machine. The care package generator 228 initially has a template care package that includes blank fields that can be customized based on the identified solution, machine information, etc. For example, when the location/type of the machine 104 to be serviced is known, the care package generator 228 can include maps corresponding to location of the machine 104 and information corresponding to the type of machine. Additionally, the care package generator 228 can provide more detailed and/or relevant information based on one or more identified error codes or one or more solutions predicted by the solution predictor 230, as further described below. For example, when the solution predictor 230 determines that the solution corresponds to a solution related to a particular part of the machine, the care package generator 228 can include manual information related to the particular part of the machine 104, replacement parts that can be needed to service the machine, and/or special tools that can be needed to service the particular part and/or the particular solution. The special tools can be tools that are not typically carried by all technicians (e.g., tools that can be included at a particular location and need to be brought to the service request). The care package generator 228 can determine whether replacement parts are needed to service the machine 104 based on feedback from technicians of previous service requests that can be stored in the problem solution database 220. In some examples, the care package generator 228 can include digital twins and/or network models (e.g., one or more artificial intelligence models) corresponding to the identified machine. Using the digital twin(s) and/or artificial intelligence model(s), the technician can be able to virtually test the model and/or digital twin before servicing the machine 104 to help ensure that the actions of the technician will fix the machine. In some examples, when the care package generator 228 determines that one or more of the solutions can be executed remotely, then the care package generator 228 can include instructions on how to service the machine 104 remotely and/or code that can be transmitted to the device to service the machine 104 remotely in the care package.

The solution predictor 230 of FIG. 2 is a structural component that predicts solutions based on identified error codes/issues in conjunction with information in the problem solution database and/or system health information. For example, the solution predictor 230 can identify potential solutions by connecting the error codes/issues to other machines based on previous solutions identified by technicians in previous surveys, by applying the errors/issues in a digital twin/model and simulating potential solutions, by identifying similar error codes/issues in other machines (e.g., based on similar models, similar contextual information, similar fleet information, similar contextual information, etc.), and/or based on the system health of the machine. Additionally or alternatively, the solution predictor 230 may implement a neural network (e.g., such as the neural network 500 of FIG. 5) to transform error codes and/or issues with problem-solution information and/or system health information to predict a solution. In such examples, the neural network may be trained using previous service request data. The solution predictor 230 transmits the identified solutions to the care package generator 228 to customize the care package based on the identified solutions.

The remote instruction executor 232 of FIG. 2 is a structural component that transmits instructions to the machine 104 (e.g., via the device interface 212) to attempt to fix the problem remotely. For example, when the care package includes instructions corresponding to a potential remote solution, then the remote instruction executor 232 can, automatically or based on instructions from a technician, transmit the instructions to the device via the device interface 212. Thus, the device can execute the instructs to see whether the remote service fixed the machine. Such remote instructions can include software updates, rebooting instructions, patches, fixes, etc.

The technician selector 234 of FIG. 2 is a structural component that selects a technician to service the request based on a plurality of factors. The technicians and relevant information of the technicians are stored in the technician database 238, as further described below. In some examples, the technician selector 234 can determine whether the service request is critical or not (e.g., based on the severity of the error codes/issues and/or based on the availability of alternative machines in the hospital). When the service request is critical, then the technician selector 234 would only select one or more technicians that are immediately available to service the machine 104 (e.g., based on the availability of the technicians and the location of the technicians with respect to the machine). In some examples, when the service request is critical, then the technician selector 234 can also take into account the tools/replacement parts needed to service request when determining the technician's distance to the machine. For example, when the service request requires a special tool/replacement part location in a particular location, then the technician selector 234 takes into account the technician's distance to the location of the special tool/replacement part. Additionally or alternatively, the technician selector 234 selects one or more technicians to service the request based on weights of the technician. The weights of the technicians correspond to how well the technician matches to the service request and is determined using the weight multiplier 236, as further described below. In some examples, the technician selector 234 analyzes the clinical work flow to see whether there are additional machines that should be serviced, will soon need to be serviced (e.g., that can be part of the problem), or are likely to have issues based on the information from the databases 216, 218, 220, 222. In some examples, the technician selector 234 may implement a neural network (e.g., the example neural network 500 of FIG. 5) to select one or more resources based on the above-inputs/resource characteristics. In such examples, the neural network may be trained based on the resources of the example technician database 238 and/or previous service request data.

The weight multiplier 236 of FIG. 2 is a structural component that weighs the available technicians for the service request. For example, the weight multiplier 236 can set an initial weight for each available technician. The weight multiplier 236 adjusts the initial weights based on various factors. For example, the factors can correspond to how many of the machines of the service request that the technicians are capable of servicing, skill level of the technicians, tools that the technicians currently possesses, replacement parts that the technician currently possess (e.g., which can be identified by the technician using the device 108), distance to the service site taking into account distance to pick up additional tools if needed, availability of the technicians, etc. The amount of weight adjustment for each factor can be based on user, manufacturer, or customer preferences.

The technician database 238 of FIG. 2 is a database that includes up-to-date information corresponding to available technicians and/or available resources, schedules of the technicians, the skill levels of the technicians, the types of machines that the technicians and/or other resources can service, the tools and/or replacement parts that the technician currently has in their possession, the location of the technicians, etc. The set of available technicians/resources can be filtered and weighted based on the information stored in the technician database 238. For example, if the problem cannot be fixed remotely, the automated resources and/or instructions/software-based resources may be filtered out. The technician information can be updated periodically, aperiodically, and-or in real-time or near real-time based on information from the technician device 108 (e.g., via the device interface 212).

The machine identifier 240 of FIG. 2 is a structural component that identifies a machine and associates the identified machine with a fleet of machines. For example, the machine identifier 240 can identify the machine 104 based on a machine identifier (e.g., an imaging device identifier, etc.) provided by the machine 104 and/or a user of the machine 104 or the machine identifier 240 can identify the machine 104 based on contextual information (e.g., by comparing location of the machine, type of machine, database information corresponding to a universe of the machines, etc., to stored system information of the enterprise system(s) database 216). In some examples, the machine identifier 240 can identify the machine 104 based on a photo submitted by a user, taken by the machine 104, taken by the technician device 108, etc., using image processing techniques. In such examples, the machine identifier 240 can compare the characteristics of the image to reference images to identify the machine 104 based on a matching reference image and/or a determined location based on the photo of the machine (e.g., by identifying the particular machine 104 based on its characteristics identified in the image, identifying its location based on features of the environment surrounding the machine 104 captured in the photo, etc.). Once the identifier is determined, the machine identifier 240 determines the make, model, modality, and/or other information of the identified machine by comparing the identifier to machine information stored in a database (e.g., the enterprise system(s) database 216, etc.). Additionally, the machine identifier 240 determines whether there is a corresponding fleet of machines. In some examples, the machine identifier 240 may implement a neural network (e.g., the example neural network 500 of FIG. 5) to identify a fleet based on an identified machine. In such examples, the neural network may be trained based on machine information corresponding to the universe of machines. A fleet of machines corresponds to a group of machines that have similar contextual information. The fleet of machines can correspond to any combination of a similar location, a similar model, a similar type, a similar climate, a similar age, similar features, etc. In some examples, a machine can correspond to multiple different fleets. Each fleet can have an artificial intelligence model (e.g., neural network model, digital twin, and/or other machine/deep learning construct, etc.) that corresponds to the fleet for applying techniques (e.g., for testing purposes) and/or identifying which solutions can solve the problem. Additionally, the machine identifier 240 can store and flag common problems among the fleet. For example, when an issue arises among a machine in the fleet, then the machine identifier 240 can store the issue as long as when the issue occurred, how long the machine 104 was operable when the issue occurred, the time from the last service etc. When the machine identifier 240 determines that the same issue occurs more than a threshold number of times in the same fleet, then the machine identifier 240 can flag the issue and transmit a warning corresponding to the flag to identify that the issue can occur in other machines of the fleet. For example, when the machine identifier 240 determines that three machines in a fleet all experienced the same issue after three years of operation, the machine identifier 240 can transmit warnings related to any machine in the fleet that has been operating for around three years. Additionally, the machine identifier 240 may update fleet information and/or generate an alert to similar machines based on issues identified by other processes (e.g., a design flaw, etc.) of the example machine recovery system 102.

The model generator 242 of FIG. 2 is a structural component to generate an artificial intelligence model (e.g., network model/digital twin, other machine/deep learning construct, etc.) when the device does not correspond to one of the fleets (e.g., does not correspond to an already available artificial intelligence model). A new fleet is created with the new artificial intelligence model and subsequent machines that correspond to the new fleet can be added to the fleet. The artificial intelligence model corresponds to the machine information (e.g., model, age, usage profile, etc.).

The survey generator 244 of FIG. 2 is a structural component that generates a survey (e.g., a prompt, flag, etc.) for a technician. The survey is provided to the technician device 108 to obtain responses from the technician after the service request is complete. In some examples, the survey is preloaded onto the technician device 108. The survey includes information related to whether the care package included all the relevant information, what information was not relevant the layout of the smart care package, were any replacement parts needed and, if so, which parts, which information should've been included but was not, which tools were used, was the identified solutions correct, where there any unexpected issues, and/or any other information that can generate more accurate smart dispatch, smart symptom, smart care package, and/or smart find processes.

The information updater 246 of FIG. 2 updates the information in the problem solution database 220 and/or the dynamic system health database 222 based on the information from the response to the survey/prompt from the technician. Additionally, the information updater 246 can update the technician database 238 based on changes of the technicians (e.g., location, tools, etc.). The information updater 246 can utilize and/or include artificial intelligence model(s) (e.g., digital twin(s), neural network(s), etc.) to perform machine learning processes to tune and improve the smart symptom, smart care package, smart dispatch, and smart find processes.

Artificial Intelligence Models

In certain examples, a target device or machine to be evaluated/repaired (e.g., an imaging device, an imaging workstation, a health information system, etc.), a resource (e.g., a technician and/or other user, a technician's device, care package, etc.), a fleet of machines, etc., can be modeled as a digital twin and/or processed according to an artificial neural network and/or other machine/deep learning network model (referred to herein as "artificial intelligence models"). Using one or more artificial intelligence models, such as a digital twin, neural network model, etc., one or more real-life system can be modeled, monitored, simulated, and prepared for field force automation management.

Digital Twin Examples

A digital representation, digital model, digital "twin", or digital "shadow" is a digital informational construct about a physical system, process, etc. That is, digital information can be implemented as a "twin" of a physical device/system/person/process and information associated with and/or embedded within the physical device/system/process. The digital twin is linked with the physical system through the lifecycle of the physical system. In certain examples, the digital twin includes a physical object in real space, a digital twin of that physical object that exists in a virtual space, and information linking the physical object with its digital twin.

The digital twin exists in a virtual space corresponding to a real space and includes a link for data flow from real space to virtual space as well as a link for information flow from virtual space to real space and virtual sub-spaces.

Figure 3:
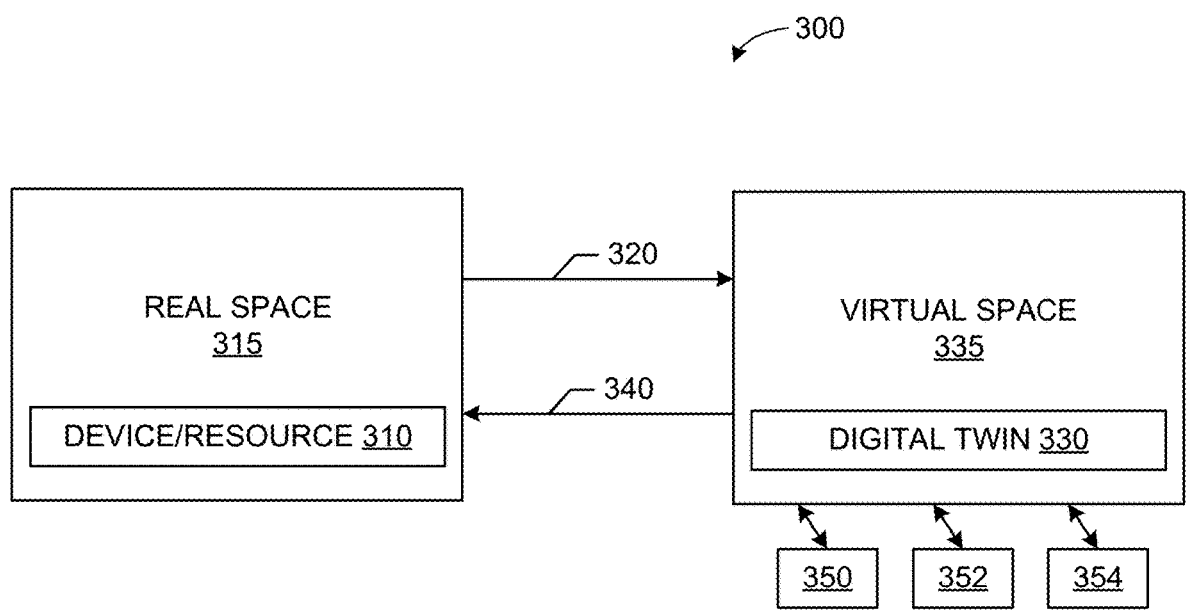
FIG. 3 is a representation of an example digital twin.

For example, FIG. 3 illustrates a machine or device such as an imaging device, radiology workstation, information system, etc.; a resource such as a technician, other user, a computing device, care package, etc.; and/or other item 310 in a real space 315 providing data 320 to a digital twin 330 in a virtual space 335. The digital twin 330 and/or its virtual space 335 provide information 340 back to the real space 315. The digital twin 130 and/or virtual space 335 can also provide information to one or more virtual sub-spaces 350, 352, 354. As shown in the example of FIG. 3, the virtual space 335 can include and/or be associated with one or more virtual sub-spaces 350, 352, 354, which can be used to model one or more parts of the digital twin 330 and/or digital "sub-twins" modeling subsystems/subparts of the overall digital twin 330.

Sensors connected to the physical object (e.g., the device/resource 310) can collect data and relay the collected data 320 to the digital twin 330 (e.g., via one or more device sensors, self-reporting, output from one or more system components such as the device interface 212, the database interface 214, the symptom processor 224, the filter 226, the care package generator 228, the solution predictor 230, the remote instruction executor 232, the technician selector 234, the weight multiplier 236, the technician database 238, the machine identifier 240, the model generator 242, the survey generator 224, the information updater 246, the database interface 246, and/or, more generally, the example machine recovery system 102, and/or combination thereof, etc.). Interaction between the digital twin 330 and the device/resource 310 can help improve detection of a symptom, determine of an issue, resolution of the issue, configuration of a tool, etc. An accurate digital description 330 of the device/resource/item 310 benefiting from a real-time or substantially real-time (e.g., accounting from data transmission, processing, and/or storage delay) allows the system 100 to predict "failures" in machine/device operation, accuracy, outcome, communication, etc.

In certain examples, sensor data, technical support, obtained images, test results, etc., can be used in augmented reality (AR) applications when a technician is examining, diagnosing, and/or otherwise fixing a machine, device, etc. (e.g., the machine 104). Using AR, the digital twin 330 follows the machine's response to the interaction with the technician, the technician device 108 and/or machine recovery system 102, for example.

Thus, rather than a generic model, the digital twin 330 is a collection of actual physics-based models reflecting the device/resource 310 (e.g., the machine 104, machine recovery system 102, technician device, etc.) and its associated norms, conditions, etc. In certain examples, three-dimensional (3D) modeling of the device/resource 310 creates the digital twin 330 for the device/resource 310. The digital twin 330 can be used to view a status of the device/resource 310 based on input data 320 dynamically provided from a source (e.g., from the device/resource 310, technician, health information system, sensor, etc.).

In certain examples, the digital twin 330 of the device/resource 310 can be used for monitoring, diagnostics, and prognostics for the device/resource 310. Using sensor data in combination with historical information, current and/or potential future conditions of the device/resource 310 can be identified, predicted, monitored, etc., using the digital twin 330. Causation, escalation, improvement, etc., can be monitored via the digital twin 330. Using the digital twin 330, the device/resource's 310 behaviors can be simulated and visualized for diagnosis, treatment, monitoring, maintenance, etc.

In contrast to computers, humans do not process information in a sequential, step-by-step process. Instead, people try to conceptualize a problem and understand its context. While a person can review data in reports, tables, etc., the person is most effective when visually reviewing a problem and trying to find its solution. Typically, however, when a person visually processes information, records the information in alphanumeric form, and then tries to re-conceptualize the information visually, information is lost and the problem-solving process is made much less efficient over time.

Using the digital twin 330, however, allows a person and/or system to view and evaluate a visualization of a situation (e.g., a device/resource 310 and associated operational problem, etc.) without translating to data and back. With the digital twin 330 in common perspective with the actual device/resource 310, physical and virtual information can be viewed together, dynamically and in real time (or substantially real time accounting for data processing, transmission, and/or storage delay). Rather than reading a report, a technician can view and simulate with the digital twin 330 to evaluate a condition, progression, possible treatment, etc., for the device/resource 310. In certain examples, features, conditions, trends, indicators, traits, etc., can be tagged and/or otherwise labeled in the digital twin 330 to allow the technician to quickly and easily view designated parameters, values, trends, alerts, etc.

The digital twin 330 can also be used for comparison (e.g., to the device/resource 310, to a "normal", standard, or reference device or resource, set of operating criteria/symptoms, best practices, protocol steps, etc.). In certain examples, the digital twin 330 of the device/resource 310 can be used to measure and visualize an ideal or "gold standard" value state for that device/resource, a margin for error or standard deviation around that value (e.g., positive and/or negative deviation from the gold standard value, etc.), an actual value, a trend of actual values, etc. A difference between the actual value or trend of actual values and the gold standard (e.g., that falls outside the acceptable deviation) can be visualized as an alphanumeric value, a color indication, a pattern, etc.

Further, the digital twin 330 of the machine/device 104 to be repaired, the technician device 108 to facilitate diagnosis/repair, etc., can facilitate collaboration among systems, technicians, etc. Using the digital twin 330, conceptualization of the device/resource 310 and its status/configuration can be shared for evaluation, modification, discussion, etc. Collaborating entities do not need to be in the same location as the device/resource 310 and can still view, interact with, and draw conclusions from the same digital twin 330, for example.

Thus, the digital twin 330 can be defined as a set of virtual information constructs that describes (e.g., fully describes) the device resource 310 from a micro level (e.g., source, detector, positioner, processor, storage, etc.) to a macro level (e.g., whole imaging device, image capture subsystem, image analysis subsystem, patient monitoring subsystem, etc.). In certain examples, the digital twin 330 can be a reference digital twin (e.g., a digital twin prototype, etc.) and/or a digital twin instance. The reference digital twin represents a prototypical or "gold standard" model of the device/resource 310 or of a particular type/category of device/resource 310, while one or more reference digital twins represent particular device(s)/resource(s) 310. Thus, the digital twin 130 of an x-ray imaging device can be implemented as a child reference digital twin organized according to certain standard or "typical" x-ray imaging device characteristics, with a particular digital twin instance representing the particular x-ray imaging device and its configuration, for example. In certain examples, multiple digital twin instances can be aggregated into a digital twin aggregate (e.g., to represent an accumulation or combination of multiple x-ray machines in a fleet sharing a common reference digital twin, etc.). The digital twin aggregate can be used to identify differences, similarities, trends, etc., between machines represented by the particular digital twin instances, for example.

In certain examples, the virtual space 335 in which the digital twin 330 (and/or multiple digital twin instances, etc.) operates is referred to as a digital twin environment. The digital twin environment 335 provides an integrated, multi-domain physics-based application space in which to operate the digital twin 330. The digital twin 330 can be analyzed in the digital twin environment 335 to predict future behavior, condition, progression, etc., of the device/resource 310, for example. The digital twin 330 can also be interrogated or queried in the digital twin environment 335 to retrieve and/or analyze current information 340, past history, etc.

In certain examples, the digital twin environment 335 can be divided into multiple virtual spaces 350-354. Each virtual space 350-354 can model a different digital twin instance and/or component of the digital twin 330 and/or each virtual space 350-354 can be used to perform a different analysis, simulation, etc., of the same digital twin 330. Using the multiple virtual spaces 350-354, the digital twin 330 can be tested inexpensively and efficiently in a plurality of ways while preserving device/resource operation and patient safety. A technician can then understand how the device/resource 310 can react to a variety of adjustments in a variety of scenarios, for example.

In certain examples, the digital twin 330 can also model a space, such as an operating room, surgical center, pre-operative preparation room, post-operative recovery room, etc. By modeling an environment, such as a surgical suite, the environment can be made, safer, more reliable, and/or more productive for patients, healthcare professionals (e.g., surgeons, nurses, anesthesiologists, technicians, etc.). For example, the digital twin 330 can be used to evaluate environmental factors (e.g., spacing, usage patterns, other equipment, etc.) that can impact machine 104 operation, etc.

In certain examples, a device, such as an optical head-mounted display (e.g., Google Glass, etc.) can be used with augmented reality to provide additional information with respect to a machine 104 being viewed, information for repair, suggestions for diagnosis, etc. The device can be used to pull in machine and/or technician device details, modeled via the digital twin 330 and verified according to manufacturer's specifications, customer machine configuration, protocol, personnel preferences, etc.

Figure 4A:
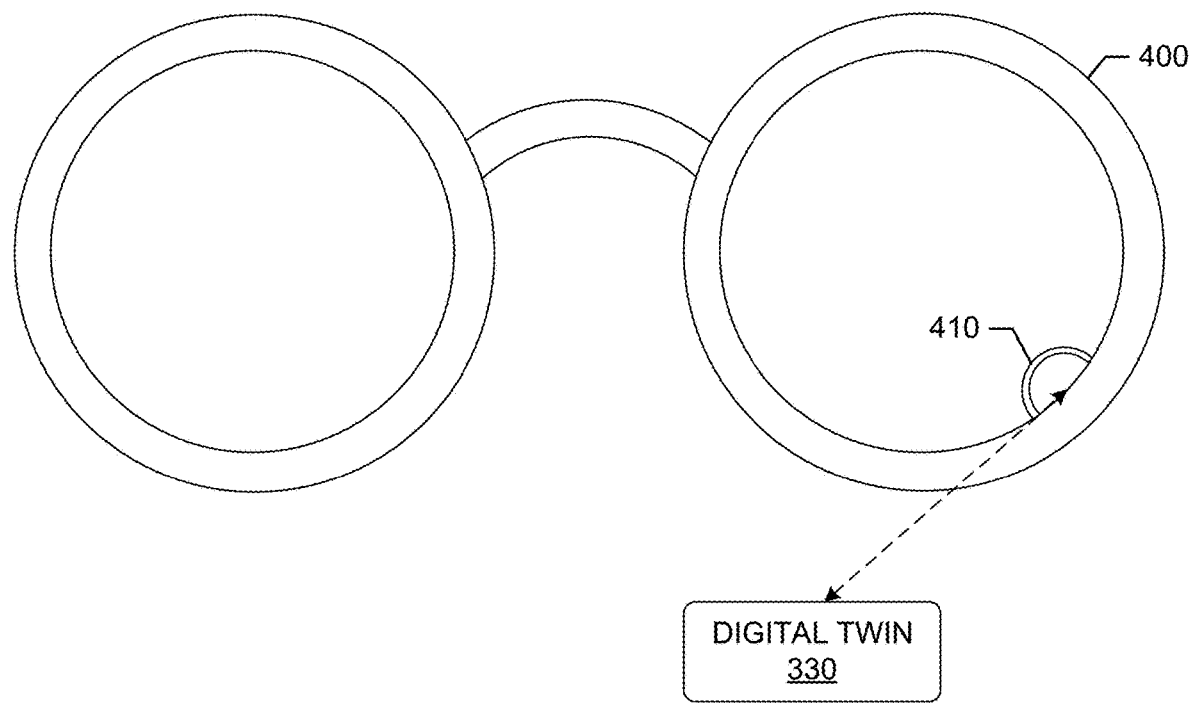
FIGS. 4A-4C depict example devices to assist in diagnosis and repair of equipment.

As shown in the example of FIG. 4A, an optical head-mounted display 400 can include a scanner or other sensor 410 that scans items in its field of view (e.g., scans barcodes, radiofrequency identifiers (RFIDs), visual profile/characteristics, etc.). In some examples, the head-mounted display 400 can be and/or can be used in conjunction with the technician device 108 of FIGS. 1A and/or 1B. Item identification, photograph, video feed, etc., can be provided by the scanner 410 to the digital twin 330, for example. The scanner 410 and/or the digital twin 330 can identify and track items within range of the scanner 410, for example. The digital twin 330 can then model the viewed environment and/or objects in the viewed environment based at least in part on input from the scanner 410, for example.

Figure 4B:
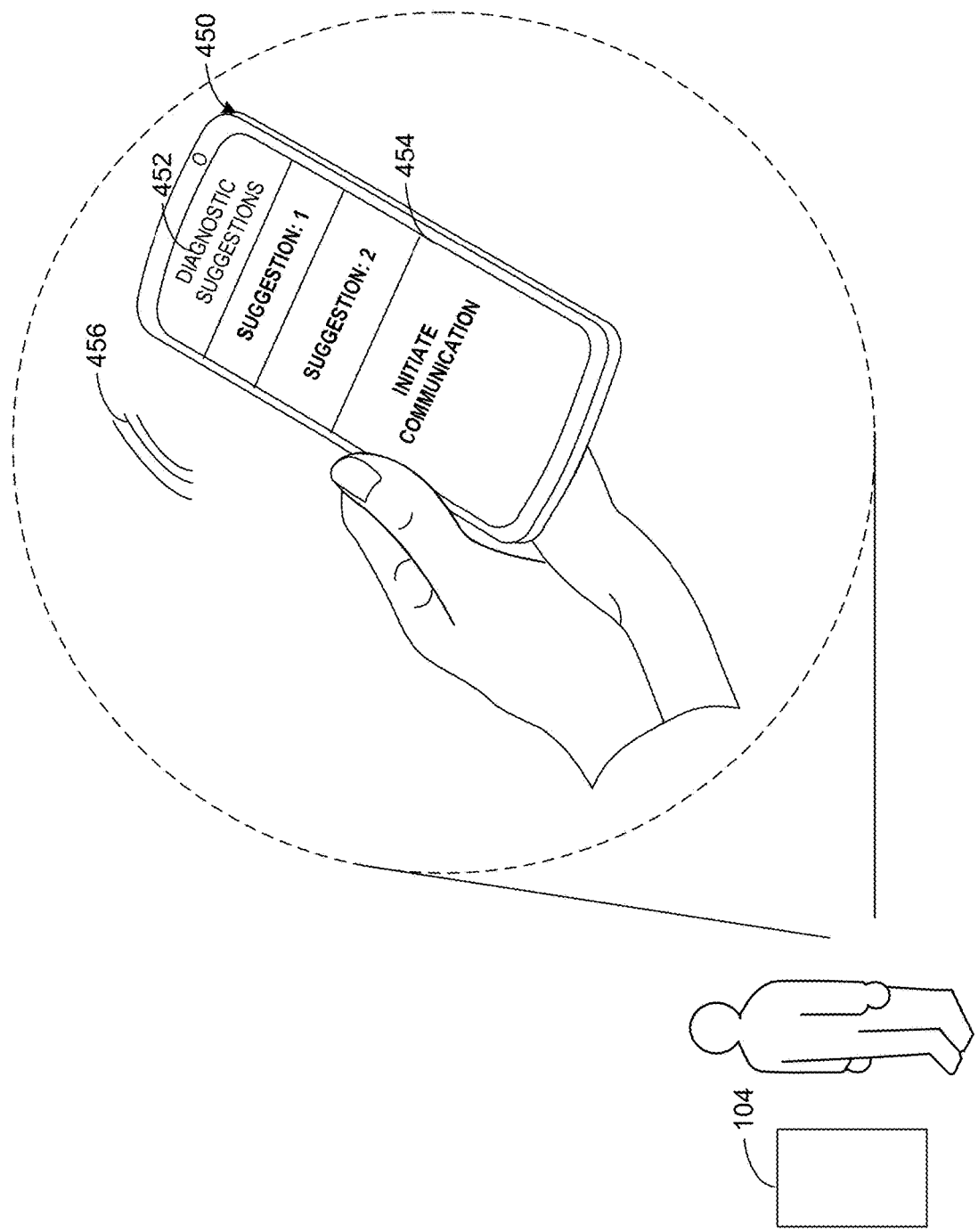

Alternatively or in addition, the digital twin 330 can be leveraged via a technician device 450, such as a smartphone, tablet computer, laptop computer, etc. In some examples, the example technician device 450 can be and/or can be used in conjunction with the technician device 108 of FIGS. 1A and/or 1B. As shown in FIG. 4B, the technician device 450 can receive input from a user, the machine recovery system 102, other diagnostic device, health information system, etc., and provide output via display to the technician, communication with the machine 104 under review, etc. For example, the technician device 450 can provide the technician with suggestions to diagnose and/or repair the machine 104. The technician device 450 can also be used to interact with the machine 104 to diagnose and/or repair issue(s) with the machine 104 and/or a related component, for example. As shown in the example of FIG. 4B, the technician device 450 can provide one or more diagnostic and/or repair suggestions 452 via a display screen 454 of the device. The example technician repair device 450 can also communicate 456 (e.g., wirelessly and/or via a wired connection) with the machine 104 to extract diagnostic information, transmit configuration setting(s), etc.

Figure 4C:
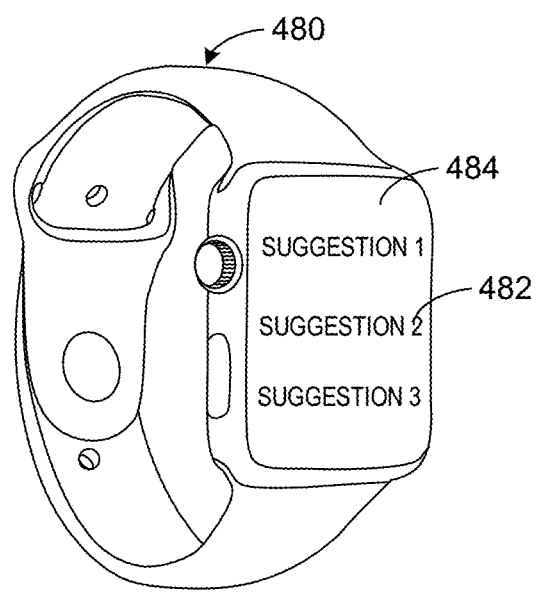

FIG. 4C illustrates an example in which suggestions, communication, prompts, other information and/or interaction, etc., is provided via a smartwatch 480 to the technician at home, en route, and/or on site. For example, one or more suggestions 482 are provided via display screen 484 of the smartwatch 480. In some examples, the example head-mounted display 480 can be and/or can be used in conjunction with the technician device 108 of FIGS. 1A and/or 1B.

Machine and/or Deep Learning Network Models

Machine learning techniques, whether deep learning networks or other experiential/observational learning systems, can be used to model information together with and/or separate from the digital twin 330 to analyze and/or predict a problem, issue, error, malfunction, etc., in a system based on log data and/or other symptom(s), predict result of particular solution(s) on particular machine(s), etc. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network (CNN) segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Alternatively or in addition to the CNN, a deep residual network can be used. In a deep residual network, a desired underlying mapping is explicitly defined in relation to stacked, non-linear internal layers of the network. Using feedforward neural networks, deep residual networks can include shortcut connections that skip over one or more internal layers to connect nodes. A deep residual network can be trained end-to-end by stochastic gradient descent (SGD) with backpropagation, for example.

Deep learning operates on the understanding that many datasets include high level features which include low level features. While examining an image of an item, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for data analysis. Stages of CNN analysis can be used for facial recognition in natural images, computer-aided diagnosis (CAD), object identification and tracking, evaluation of symptoms, evaluation of remediation outcomes, etc.

Deep learning machines can provide computer aided detection support to improve item identification, relevance evaluation, and tracking, for example. Supervised deep learning can help reduce susceptibility to false classification, for example. Deep learning machines can utilize transfer learning when interacting with technicians to counteract the small dataset available in the supervised training. These deep learning machines can improve their protocol adherence over time through training and transfer learning.

Figure 5:
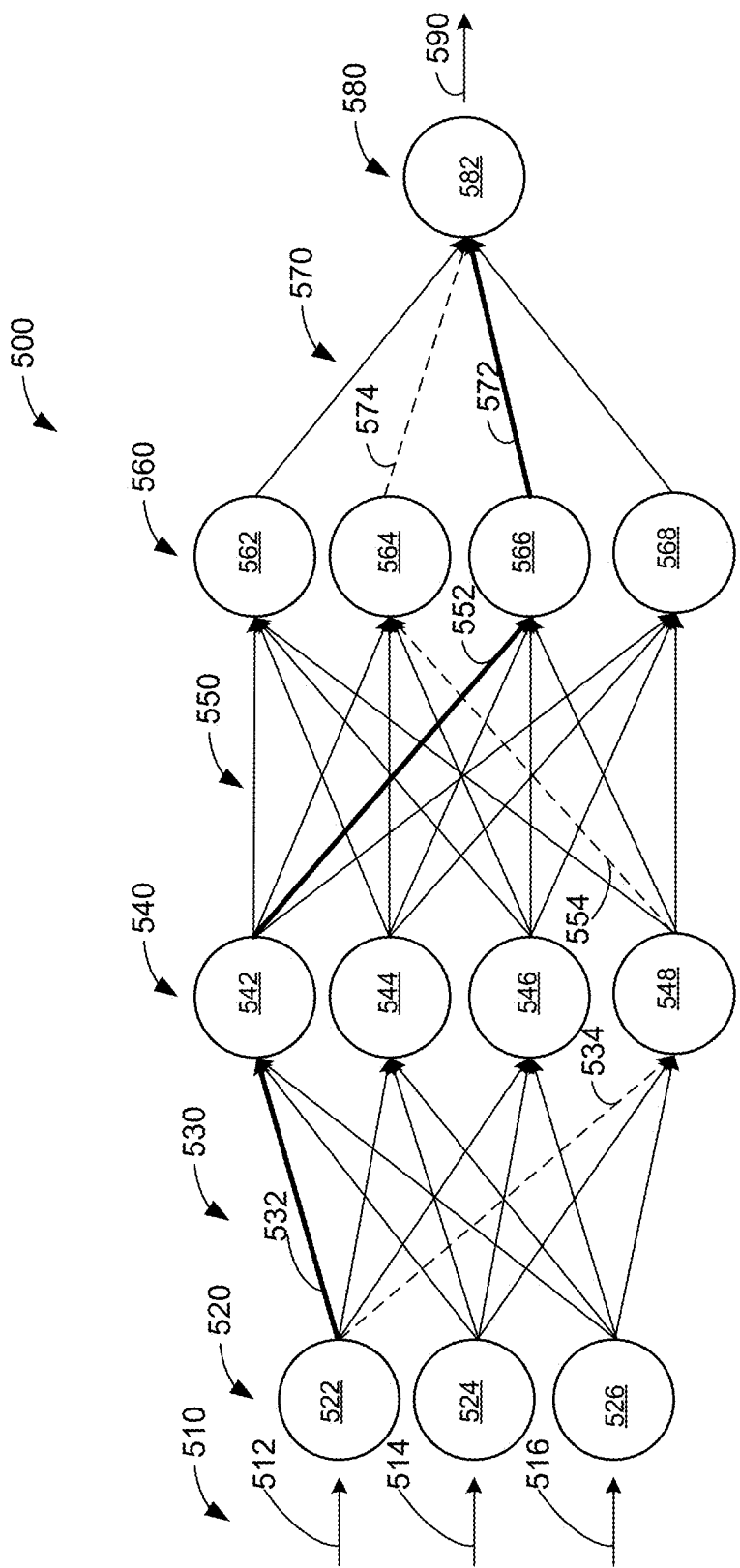
FIG. 5 is a representation of an example deep learning neural network model.

FIG. 5 is a representation of an example deep learning neural network model 500 that can be used to implement the digital twin 330, work with the digital twin 330 to provide suggestions for diagnosis and/or repair, and/or operate instead of the digital twin 330 to generate suggested issues based on input symptoms, provide suggested repairs based on input machine configuration and problem information, etc. The example neural network 500 includes layers 520, 540, 560, and 580. The layers 520 and 540 are connected with neural connections 530. The layers 540 and 560 are connected with neural connections 550. The layers 560 and 580 are connected with neural connections 570. Data flows forward via inputs 512, 514, 516 from the input layer 520 to the output layer 580 and to an output 590. In some examples, the neural network model 500 is included in and/or utilized by one or more of the components the machine recovery system 102 of FIG. 2.

The layer 520 is an input layer that, in the example of FIG. 5, includes a plurality of nodes 522, 524, 526. The layers 540 and 560 are hidden layers and include, the example of FIG. 5, nodes 542, 544, 546, 548, 562, 564, 566, 568. The neural network 500 can include more or less hidden layers 540 and 560 than shown. The layer 580 is an output layer and includes, in the example of FIG. 5, a node 582 with an output 590. Each input 512-516 corresponds to a node 522-526 of the input layer 520, and each node 522-526 of the input layer 520 has a connection 530 to each node 542-548 of the hidden layer 540. Each node 542-548 of the hidden layer 540 has a connection 550 to each node 562-568 of the hidden layer 560. Each node 562-568 of the hidden layer 560 has a connection 570 to the output layer 580. The output layer 580 has an output 590 to provide an output from the example neural network 500.

Of connections 530, 550, and 570 certain example connections 532, 552, 572 can be given added weight while other example connections 534, 554, 574 can be given less weight in the neural network 500. Input nodes 522-526 are activated through receipt of input data via inputs 512-516, for example. Nodes 542-548 and 562-568 of hidden layers 540 and 560 are activated through the forward flow of data through the network 500 via the connections 530 and 550, respectively. Node 582 of the output layer 580 is activated after data processed in hidden layers 540 and 560 is sent via connections 570. When the output node 582 of the output layer 580 is activated, the node 582 outputs an appropriate value based on processing accomplished in hidden layers 540 and 560 of the neural network 500.

While an example implementation of the machine recovery system 102 of FIGS. 1A and/or 1B is illustrated in FIG. 2, one or more of the elements, processes and/or devices illustrated in FIG. 2 can be combined, divided, re-arranged, omitted, eliminated and/or implemented in any other way. Further, the device interface 212, the database interface 214, the symptom processor 224, the filter 226, the care package generator 228, the solution predictor 230, the remote instruction executor 232, the technician selector 234, the weight multiplier 236, the technician database 238, the machine identifier 240, the model generator 242, the survey generator 224, the information updater 246, the database interface 246, and/or, more generally, the machine recovery system 102 of FIG. 2 can be implemented by hardware, software, firmware and/or any combination of hardware, software and/or firmware. Thus, for example, any of the device interface 212, the database interface 214, the symptom processor 224, the filter 226, the care package generator 228, the solution predictor 230, the remote instruction executor 232, the technician selector 234, the weight multiplier 236, the technician database 238, the machine identifier 240, the model generator 242, the survey generator 224, the information updater 246, the database interface 246, and/or, more generally, the machine recovery system 102 of FIG. 2 could be implemented by one or more analog or digital circuit(s), logic circuits, programmable processor(s), programmable controller(s), graphics processing unit(s) (GPU(s)), digital signal processor(s) (DSP(s)), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the device interface 212, the database interface 214, the symptom processor 224, the filter 226, the care package generator 228, the solution predictor 230, the remote instruction executor 232, the technician selector 234, the weight multiplier 236, the technician database 238, the machine identifier 240, the model generator 242, the survey generator 224, the information updater 246, and/or the database interface 246 is/are hereby expressly defined to include a non-transitory computer readable storage device or storage disk such as a memory, a digital versatile disk (DVD), a compact disk (CD), a Blu-ray disk, etc. including the software and/or firmware. Further still, the machine recovery system 102 of FIG. 2 can include one or more elements, processes and/or devices in addition to, or instead of, those illustrated in FIG. 2, and/or can include more than one of any or all of the illustrated elements, processes and devices. As used herein, the phrase "in communication," including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

Flowcharts representative of example hardware logic, machine readable instructions, hardware implemented state machines, and/or any combination thereof for implementing the machine recovery system 102 of FIG. 2 are shown in FIGS. 6-10. The machine readable instructions can be an executable program or portion of an executable program for execution by a computer processor such as the processor 1112 shown in the processor platform 800 discussed below in connection with FIG. 11. The program can be embodied in software stored on a non-transitory computer readable storage medium such as a CD-ROM, a floppy disk, a hard drive, a DVD, a Blu-ray disk, or a memory associated with the processor 1112, but the entire program and/or parts thereof could alternatively be executed by a device other than the processor 1112 and/or embodied in firmware or dedicated hardware. Further, although the example program is described with reference to the flowcharts illustrated in FIGS. 6-10, many other methods of implementing the machine recovery system 102 can alternatively be used. For example, the order of execution of the blocks can be changed, and/or some of the blocks described can be changed, eliminated, or combined. Additionally or alternatively, any or all of the blocks can be implemented by one or more hardware circuits (e.g., discrete and/or integrated analog and/or digital circuitry, an FPGA, an ASIC, a comparator, an operational-amplifier (op-amp), a logic circuit, etc.) structured to perform the corresponding operation without executing software or firmware.

As mentioned above, the example processes of FIGS. 6-10 can be implemented using executable instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media.

"Including" and "comprising" (and all forms and tenses thereof) are used herein to be open ended terms. Thus, whenever a claim employs any form of "include" or "comprise" (e.g., comprises, includes, comprising, including, having, etc.) as a preamble or within a claim recitation of any kind, it is to be understood that additional elements, terms, etc. can be present without falling outside the scope of the corresponding claim or recitation. As used herein, when the phrase "at least" is used as the transition term in, for example, a preamble of a claim, it is open-ended in the same manner as the term "comprising" and "including" are open ended. The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used in the context of describing the performance or execution of processes, instructions, actions, activities and/or steps, the phrase "at least one of A or B" is intended to refer to implementations including any of (1) at least one A, (2) at least one B, and (3) at least one A and at least one B.

Figure 6:
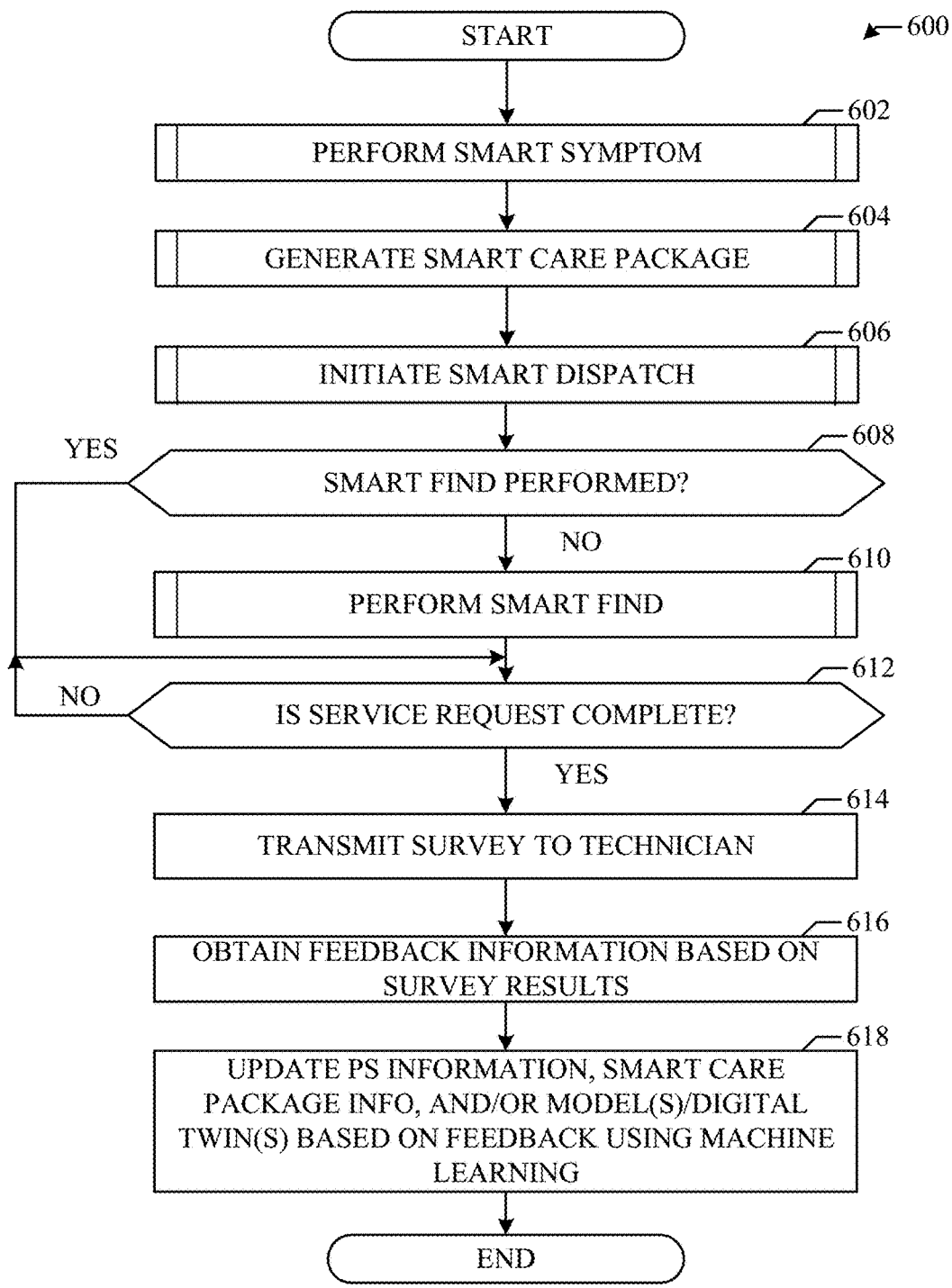
FIG. 6 is a flowchart representative of machine readable instructions which can be executed to implement the machine recovery system of FIGS. 1A and/or 1B to handle a service request from a machine of FIGS. 1A and/or 1B.

FIG. 6 includes a flowchart 600 representative of machine readable instructions that can be implemented by the structural components of the machine recovery system 102 of FIG. 2. Although the flowchart 600 of FIG. 6 is described in conjunction with the machine recovery system 102 of FIGS. 1 and/or 2, other type(s) of recovery system(s) and/or other type(s) of processor(s) can be utilized instead.

At block 602, the smart symptom system 202 of the machine recovery system 102 performs the smart symptom process. As further described below in conjunction with FIG. 7, the smart symptom system 202 converts symptoms of a machine to issues and/or error codes for to service the machine. At block 604, the smart care package system 204 of the machine recover system 102 performs the smart care package process. As further described below in conjunction with FIG. 8, the smart care package system 204 generates a smart care package to the device 108 of the technician to service the machine 104. At block 606, the smart dispatch system 206 of the machine recover system 102 performs the smart dispatch process. As further described below in conjunction with FIG. 9, the smart dispatch system 206 performs the smart dispatch to select one or more technicians to service the machine.

At block 608, the smart find system 208 of the machine recover system 102 determines whether the smart find process has been performed within one of the previous processes (e.g., the smart symptom, the smart care package, and/or the smart dispatch processes). When the smart find process was not performed during the initial processes, then the smart find can be performed in conjunction with the technician servicing the request. For example, the technician can enter information into the technician device 108 during the servicing to identify the machine. When the smart find system 208 determines that a smart find process has been performed (block 608: YES), then the process continues to block 612. When the smart find system 208 determines that a smart find process has not been performed (block 608: NO), then the smart find system 208 performs a smart find process (block 610), as further described below in conjunction with FIG. 10.

At block 612, the survey generator 244 determines whether the service request is complete. For example, when the technician completes a service request, the technician can identify the completion via the technician device 108, which transmits a completion trigger via the device interface 212. The survey generator 244 determines that the service request is complete in response to receiving the completion trigger. When the survey generator 244 determines that the service request is not complete (block 612: NO), then the process returns to block 612 until the service request is complete. When the survey generator 244 determines that the service request is complete (block 612: YES), then the survey generator 244 transmits a generated survey to the technician device 108 via the device interface 212 (block 614). Alternatively, the prompt may be preloaded into the technician device 108. In such an example, the survey generator 244 does not transmit the survey. Rather, the survey generator 244 determines that the service request is complete when the feedback from the preloaded prompt is received at the machine recovery system 102. At block 616, the information updater 246 obtains feedback information based on the survey results entered by the technician (e.g., via the device interface 212). At block 618, the information updater 246 updates the problem solution information in the problem solution database 220, smart care package format and/or provided information, and/or the artificial intelligence model(s) (models/digital twins, neural networks, etc.) based on the feedback using the artificial network model(s) to perform machine learning. For example, the neural network 800 of FIG. 8 can be utilized to implement the digital twin 630, work with the digital twin 630 to provide suggestions for diagnosis and/or repair, and/or operate instead of the digital twin 630 to generate suggested issues based on input symptoms, provide suggested repairs based on input machine configuration and problem information, etc. to update data in the databases 216, 218, 220, 222, 238 and/or update the digital twins and/or optimize the smart symptom process, smart care package process, smart dispatch process, and/or smart find process for future service requests by applying the obtained feedback data to the neural network (e.g., to further train the neural network).

Figure 7:
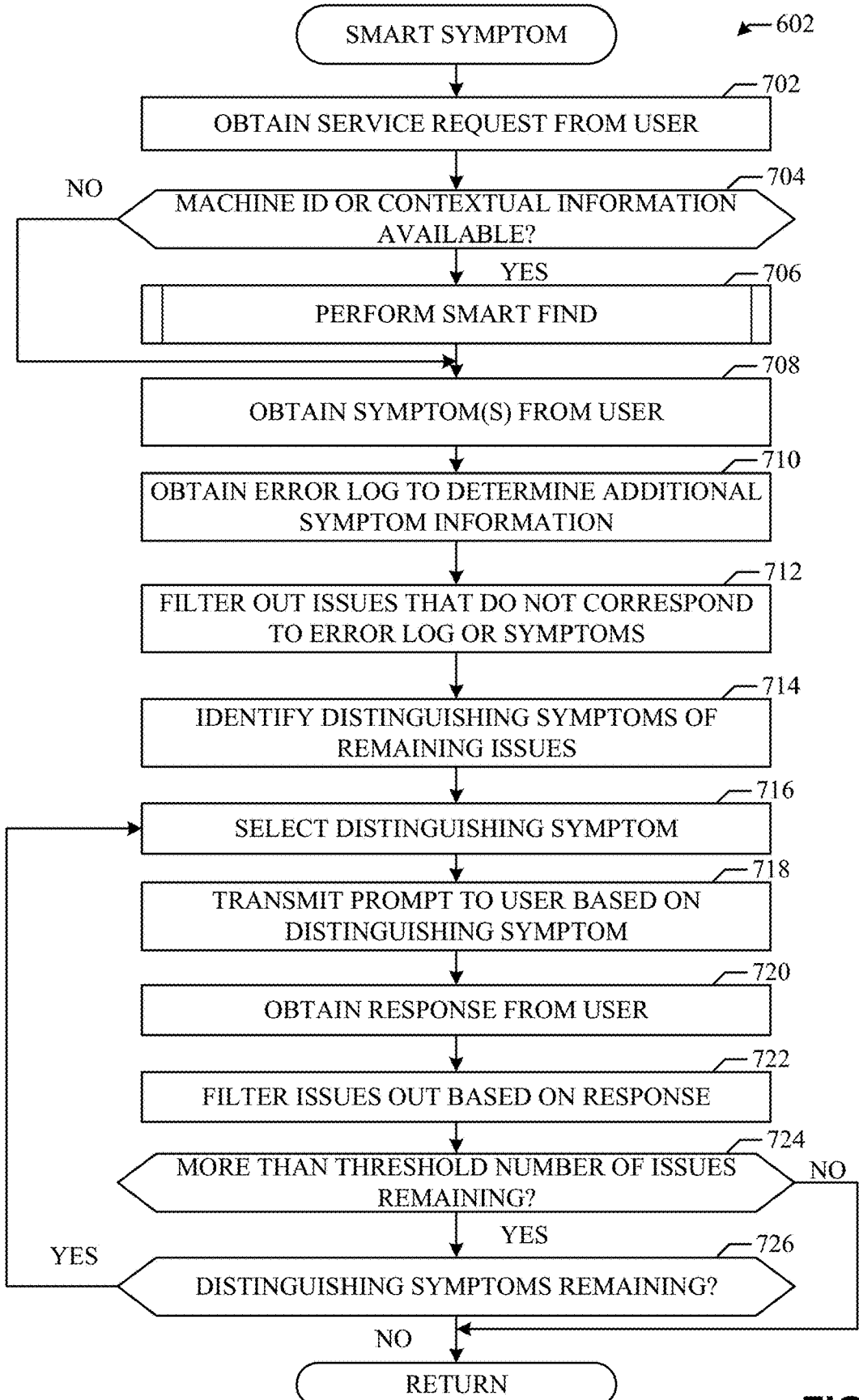
FIG. 7 is a flowchart representative of machine readable instructions which can be executed to implement the machine recovery system of FIGS. 1A and/or 1B to perform a smart symptom process.

FIG. 7 includes a flowchart 602 representative of machine readable instructions that can be implemented by the structural components of the machine recovery system 102 of FIG. 2 to perform a smart symptom process. Although the flowchart 602 of FIG. 7 is described in conjunction with the machine recovery system 102 of FIGS. 1 and/or 2, other type(s) of recovery system(s) and/or other type(s) of processor(s) can be utilized instead.

At block 702, the symptom processor 224 obtains a service request from a user via the device interface 212. For example, a user can call into a service center 106 that transmits the service request to the device interface 212 or the user can enter the service request on a user interface on a computer or on the machine 104 itself that is transmitted, directly or indirectly, to the device interface 212. At block 704, the machine identifier 240 determines whether a machine identifier or image device identifier and/or contextual information is available for the machine. For example, when the user interfaces with a user interface on the machine 104 and the machine 104 transmits the service request, then the machine 104 can include additional information including the machine/imaging device ID and/or contextual information.

If the machine identifier 240 determines that the machine/imaging device ID or contextual information is not available (block 704: NO), then the process continues to block 708. When the machine identifier 240 determines that the machine/imaging device ID or contextual information is available (block 704: YES), then the machine recovery system 102 performs the smart find process (block 706), as further described below in conjunction with FIG. 10. At block 708, the symptom processor 224 obtains one or more symptoms from the user via the device interface 212. The one or more symptoms can be included in the service request. In some examples, the service request may not include any symptoms. At block 710, the symptom processor 224 obtains error log (e.g., logs identifying one or more error codes) information from the machine log database 218 corresponding to the machine. At block 712, the filter 226 filters out issues that do not correspond to the error logs and/or symptoms to generate a subset of issues that correspond to the error logs and/or symptoms. The filter 226 obtains the issues from the issue database 227.

At block 714, the symptom processor 224 identifies distinguishing symptoms of remaining issues. For example, the symptom processor 224 can identify a distinguishing symptom to split the issues into first issues that correspond to the distinguishing symptom and second issues that do not correspond to the distinguishing symptoms. The symptom processor 224 can identify whether one or more of the distinguishing features is present in the machine 104, and the filter 226 can filter out the first or second issues based on system feedback and/or user response to reduce the number of potential issues that a technician is to check/fix to service for the machine 104.

At block 716, the symptom processor 224 selects a distinguishing symptom. The symptom processor 224 can select a symptom that is most distinguishing (e.g., a symptom that corresponds to as close to half of the remaining issues). At block 718, the symptom processor 224 transmits a prompt to the machine, a user and/or a user device (e.g., the computing device used by the user to transmit data corresponding to the machine) based on the distinguishing symptom via the device interface 212. The prompt can be sent directly to the machine 104 and/or to the service center 106 (e.g., which then instructs the machine, the user, and/or user device based on the prompt). In some examples, the prompt is preloaded on the technician device 108. The prompt requests a response from the machine, user, and/or technician device 108 to identify whether the selected distinguishing symptom is present and/or to perform a process to see whether the distinguishing symptom is present. For example, the prompt can include instructions to be performed automatically by the machine for the machine to provide additional feedback corresponding to additional symptoms (e.g., instructions to execute one or more processes and provide the results of the one or more processes as feedback). In another example, the prompt can identify distinguishing symptoms to a user device (e.g., a computer or computing device) that prompts the user for additional feedback corresponding to the distinguishing symptom. In some examples, the technician device 108 can obtain data directly or indirectly from the machine 104 and include the obtained data in the feedback (e.g., input data and/or output data from different parts of the machine 104 taken before, during, and/or after the servicing).

At block 720, the symptom processor 224 obtains a response from the user (e.g., directly via the machine 104 or via the service center 106) and/or from machine (e.g., without input from the user) via the device interface 212. The response includes data related to whether or not the distinguishing symptom is present at the machine. At block 722, the filter 226 filters out issues based on the response. For example, when the response indicates that the distinguishing symptom is present in the machine, then the filter 226 filters out the issues that do not correspond to the distinguishing symptom and when the response indicates that the distinguishing symptom is not present in the machine, the filter 226 filters out the issues that do correspond to the distinguishing symptom.

At block 724, the symptom processor 224 determines whether more than a threshold number of issues are remaining. The threshold number of issues can be based on user and/or manufacturer preferences, for example. When the symptom processor 224 determines that there are not more than a threshold number of issues remaining (block 724: NO), then the process returns to block 604 of FIG. 6. When the symptom processor 224 determines that there are more than a threshold number of issues remaining (block 724: YES), then the symptom processor 224 determines whether there are additional distinguishing symptoms remaining (block 726). When the symptom processor 224 determines that there are additional distinguishing symptoms remaining (block 726: YES), then the process returns to block 716 to further filter out issues. When the symptom processor 224 determines that there are no additional distinguishing symptoms remaining (block 726: NO), then the process returns to block 604 of FIG. 6.

Additionally or alternatively, the symptom processor 224 of FIG. 2 can interface with the machine 108 (e.g., directly using the device interface 212 and/or indirectly via the technician device 108) to obtain output data of the machine 104 (e.g., photos taken by the machine 104). In such examples, the symptom processor 224 can process an image obtained by the imaging device to identify an artifact (e.g., flaw) found on the image. The symptom processor 224 can uses identified flaws to identify a problem, a source of the problem, and/or additional symptoms. For example, the symptom processor 224 can, based on an identified flaw, determine that that there is not enough radiation, too much radiation, identify a failing detector, misalignment issues, etc. In some examples, the symptom processor 224 can compare the identified problem, source of problem, and/or symptoms associated with the flaw with previous problem-solution information (e.g., stored in the example problem solution database 220), to determine if the problem corresponds to a configuration and/or design flaw. In such examples, the symptom processor 224 may transmit an alert to the machine 108, a user of the machine 108 (e.g., via text, email, etc.), a system administrator, etc. identify the design flaw. Additionally, the machine identifier 240 may update fleet information and/or generate an alert to similar machines to identify the design flaw.

Figure 8:
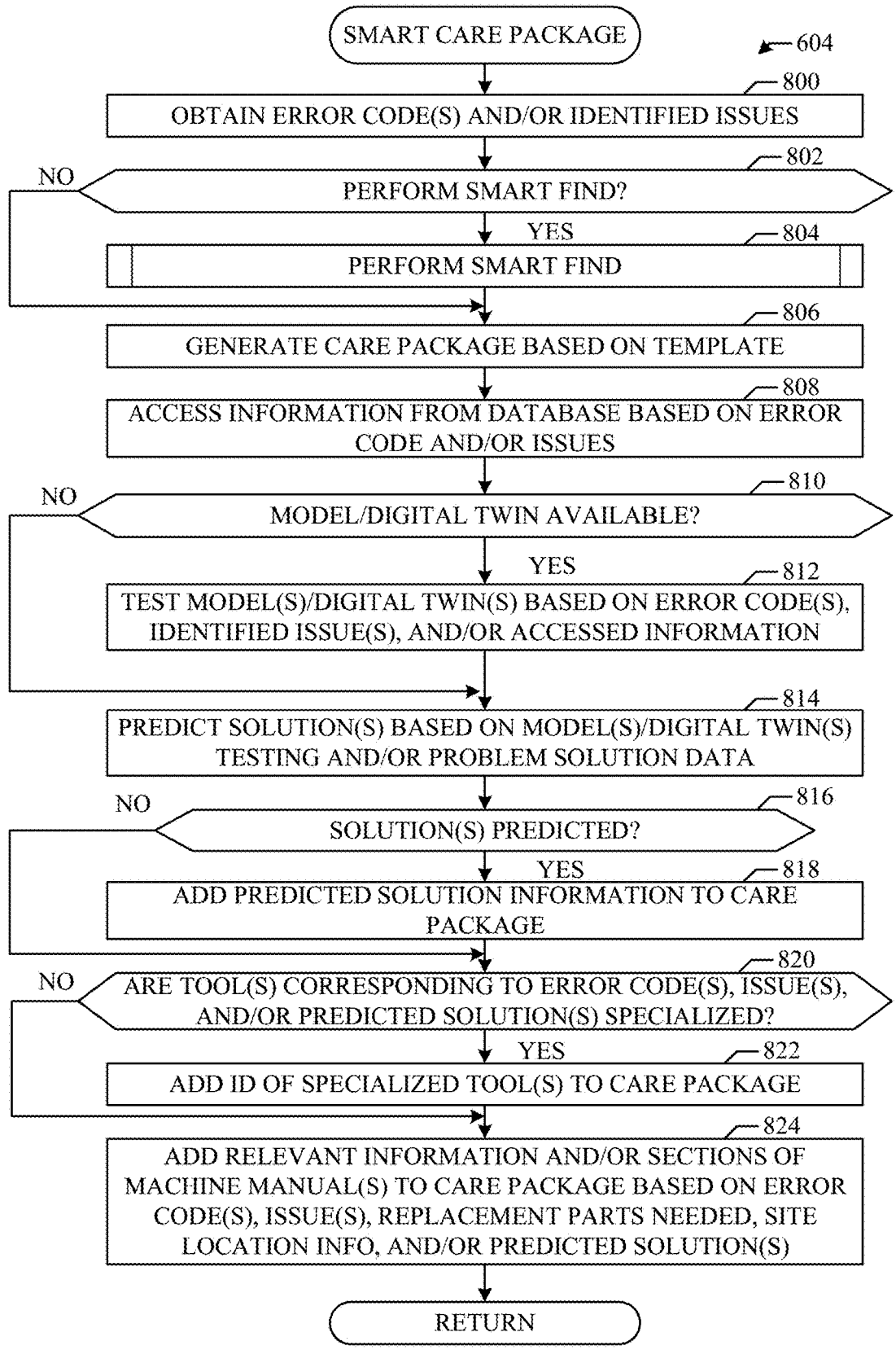
FIG. 8 is a flowchart representative of machine readable instructions which can be executed to implement the machine recovery system of FIGS. 1A and/or 1B to perform a smart care package process.

FIG. 8 includes a flowchart 604 representative of machine readable instructions that can be implemented by the structural components of the machine recovery system 102 of FIG. 2 to perform a smart care package process. Although the flowchart 604 of FIG. 8 is described in conjunction with the machine recovery system 102 of FIGS. 1 and/or 2, other type(s) of recovery system(s) and/or other type(s) of processor(s) can be utilized instead.

At block 800, the care package generator 225 obtains error code(s) (e.g., from the machine log(s) database 218 via the database interface 214) and/or indemnified issues from the symptom processor 224. In some examples, the machine log(s) 218 can include machine identifiers and/or contextual information that can be used to perform a smart find process. At block 802, the machine identifier 240 determines whether a smart find should be performed. For example, the machine identifier 240 can perform a smart process when the smart find process has yet to be performed and the error code(s) provide additional information (e.g., machine identifiers and/or particular contextual information) for the smart find process to be performed.

When the machine identifier 240 determines that the smart find is not to be performed (block 802: NO), then the process continues to block 806. When the machine identifier 240 determines that the smart find process should be performed (block 802: YES), then the machine recovery system 102 performs the smart find process (block 804), as further described below in conjunction with FIG. 10. At block 806, the care package generator 228 generates a care package based on a template layout. The initial template layout can be based on technician and/or manufacturer preferences and can be customizable. At block 808, the care package generator 228 accesses information from the databases 216, 220, 222 via the database interface 214. For example, the care package generator 228 can access (A) contextual information (e.g., customer site and layout information, contract warranty, asset location, historical machine information, etc.) from the enterprise system(s) database 216 when the machine 104 has been identified, (B) problem solution data corresponding to the error code(s) and/or identified issues from the problem solution database 220, and/or (C) system health information corresponding to the machine 104 from the dynamic system health database 222.

At block 810, the care package generator 204 determines whether a model/digital twin corresponding to the machine 104 is available. For example, when the smart find process has been performed, then a model/digital twin corresponding to the machine 104 has already been identified. Additionally or alternatively, a model/digital twin can be selected based on the error code(s), identified issues, and/or accessed information. When the care package generator 204 determines that a model/digital twin corresponding to the machine 104 is not available (block 810: NO), then the process continues to block 814. When the care package generator 204 determines that a model/digital twin corresponding to the machine 104 is available (block 810: YES), then the solution predictor 230 tests the corresponding model(s)/digital twin(s) based on error code(s), identified issue(s), and/or accessed information to identify potential solutions to the problem(s) of the machine.

For example, a digital twin of an x-ray imaging device and/or of a component of the x-ray imaging device (e.g., a digital twin of an x-ray detector, etc.) can be processed based on symptom(s) and/or other information. The digital twin models the symptom(s) to determine associated system issue(s) and/or models the issue(s) to simulate one or more solutions and associated outcome(s) to help determine a solution or "fix" to be applied to ameliorate the symptom(s) exhibited by the machine 104, for example. Since the digital twin is a physics-based model or replica of the actual machine 104 and its environment, reproduced in virtual space, an impact on the digital twin should indicate a similar impact on the actual machine 104.

Alternatively or in addition, a deep learning network, such as the deep learning network 500, can be applied to take as inputs the symptom(s), issue(s), configuration information for the machine 104, etc., and correlate those inputs with resource constraints, customer requirements, machine limitations, etc., to determine a proposed solution to address the issue(s), for example.

At block 814, the solution predictor 230 predicts solution(s) based on the testing of the artificial intelligence model(s) (e.g., model(s)/digital twin(s), neural network(s), etc.) and/or problem solution data of the problem solution database 220 that corresponds to the obtained error code(s), identified issue(s), and/or accessed information. At block 816, the solution predictor 230 determines whether at least one solution was able to be predicted. When at least one solution was not able to be predicted (block 816: NO), then the process continues to block 820. When at least one solution was able to be predicted (block 816: YES), then the care package generator 228 adds the predicted solution information to the care package (block 818). For example, the care package generator 228 can add parts of manual(s)/tutorial(s) corresponding to the predicted solution.

At block 820, the care package generator 228 determines whether there are tools corresponding to the error code(s), issue(s), and/or predicted solution(s) that are specialized tools. For example, every technician can carry or be required to carry certain tools and can be permitted to not carry specialized tools that are either too large to carry around all the time, are rarely utilized, and/or are too expensive for a company to purchase a specialized tool for each technician. Accordingly, some specialized tools can be located in a predetermined location where a technician can obtain the specialized tool when needed. Accordingly, it is preferable to know whether a service request is going to need a specialized tool, so that the technician can arrive with the tool, as opposed to finding out that he/she needs the tool after already arriving at the service location. The correspondence between a specialized tool and an error code, issue, and/or predicted solution can be stored in the problem solution database 220.

If the care package generator 228 determines that one or more tool(s) corresponding to the error code(s), issue(s), and/or predicated solution(s) is not a specialized tool (block 820: NO), the process continues to block 824. When the care package generator 228 determines that one or more tool(s) corresponding to the error code(s), issue(s), and/or predicated solution(s) is a specialized tool (block 820: YES), the care package generator 228 adds an identifier of the specialized tool(s) to the care package (block 822). Thus, the technician is made aware that he/she can need to obtain the specialized tool for the service request. At block 824, the care package generator 228 adds other relevant information and/or sections of machine manual(s)/tutorial(s) to the care package base on the error code(s), issue(s), replacement part(s) that can be needed, site location information (e.g., map(s) and/or directions to the site location), and/or predicted solution(s).

The final care package is a data structure of relevant customer data, machine configuration information, executable instructions/code, etc., that can be used by a resource to fix and/or identify a problem of the machine 104. When the problem may be fixed remotely (e.g., automatically by transmitting instructions to be executed by the machine 104), the care package may include software instructions, patches, etc. that may be transmitted to the machine 104 for repair and/or to prompt additional data corresponding to the problem. Additionally, the care package may include software that, when executed by the machine 104 identifies whether or not the problem and/or other problems have been fixed. When the care package is being transmitted to technician device 108 of a technician, the care package is a data structure that includes relevant and customized data that a technician may need to avoid unnecessary down time, expense, etc. For example, the care package allows the technician to identify replacement parts, specialized tools, etc., that are needed to service the request before reaching the location. Additionally, the care package has identified relevant sections of service manuals, so that the technician does not have to spend time and effort finding the correct manual information corresponding to a machine and/or problem. Additionally, the care package eliminates a new technician looking up incorrect information when servicing the machine 104. Additionally, when the care package includes a digital twin, the technician can avoid doing further damage to the machine and/or avoid wasting time on unsuccessful service techniques by applying techniques to the digital twin first.

Figure 9:
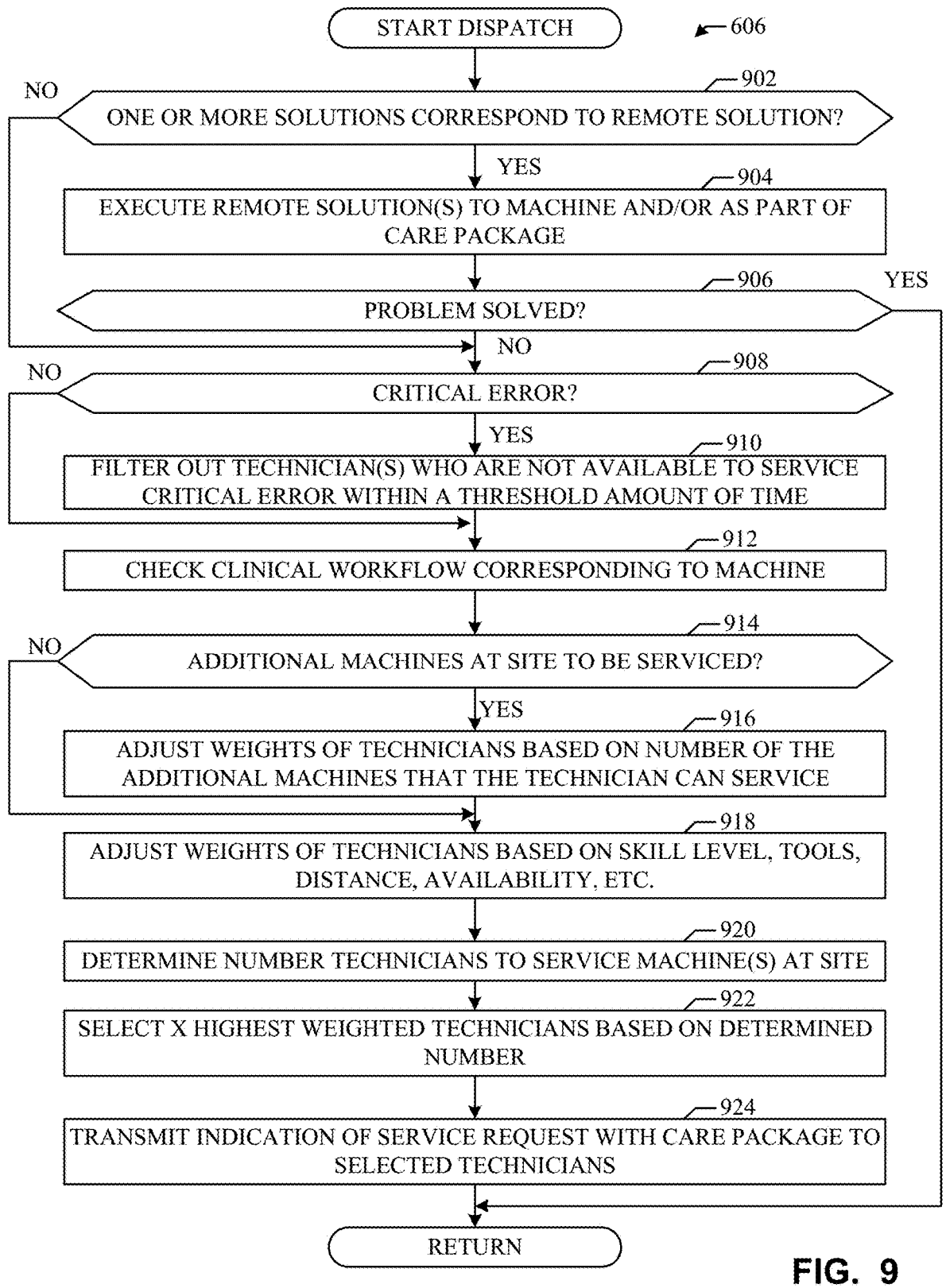
FIG. 9 is a flowchart representative of machine readable instructions which can be executed to implement the machine recovery system of FIGS. 1A and/or 1B to perform a smart dispatch.

FIG. 9 includes a flowchart 606 representative of machine readable instructions that can be implemented by the structural components of the machine recovery system 102 of FIG. 2 to perform a smart dispatch process. Although the flowchart 606 of FIG. 9 is described in conjunction with the machine recovery system 102 of FIGS. 1 and/or 2, other type(s) of recovery system(s) and/or other type(s) of processor(s) can be utilized instead.

At block 902, the remote instruction executor 232 determines whether one or more of the identified solution(s) corresponds to (e.g., can be fixed via) one or more remote solution(s). For example, the problem solution database 220 can include information relating to previous problems that have been solved or could be solved with remote instruction(s). Accordingly, the remote instruction executor 232 can access the problem solution database 220 via the database interface 214 using the identified solutions to determine whether one or more of the identified solutions can be fixed remotely. When the remote instruction executor 232 determines that one or more solutions do not correspond to a remote solution (block 902: NO), then the process continues to block 908. When the remote instruction executor 232 determines that one or more solutions correspond to a remote solution (block 902: YES), then the remote instruction executor 232 executes the remote solutions(s) to the machine 104 (e.g., directly) and/or as part of a care package to the technician (block 904). For example, the remote instruction executor 232 can transmit a software patch, reboot instructions, and/or other remote instructions to attempt to solve one or more of the problems affecting the machine. In another example, the remote instruction executor 232 alerts the technician to the potential remote instruction solution via the care package. In such an example, the technician attempts to transmit instructions to the machine 104 remotely to attempt to solve the problem.

At block 906, the remote instruction executor 232 determines whether the problem with the machine 104 has been solved. For example, the remote instruction executor 232 can determine that the problem with the machine 104 has been solved based on network communications directly with the machine 104 and/or based on a completion trigger and/or any other trigger from the technician device 108 identifying that the service request is complete. When the remote instruction executor 232 determines that the problem has been solved (block 906: YES), then the process returns to block 608 of FIG. 6. When the remote instruction executor 232 determines that the problem has not been solved (block 906: NO), then the process continues to block 908.

At block 908, the technician selector 234 determines whether the identified error code(s) and/or issue(s) correspond to a critical error. Error codes and/or issues can be identified as critical error(s) based on user/manufacture/customer preferences. For example, when a customer has two of the same machine, any error code from one machine is not critical, so long as the other machine is operational. In another example, any error code and/or issue that results in total shut down of the machine 104 can correspond to a critical error. When the technician selector 234 determines that the identified error code(s) and/or issue(s) does not correspond to a critical error (block 908: NO), then the process continues to block 912. When the technician selector 234 determines that the identified error code(s) and/or issue(s) correspond to a critical error (block 908: YES), then the technician selector 234 generates a group of available technicians by filtering out technician(s) in the technician database 238 who are not available to service the critical error within a threshold amount of time (block 910). For example, the technician selector 234 can analyze the schedules of the technicians to determine which technicians are immediately available (e.g., can service the request within a threshold amount of time based on their schedule and their distance to the service location, etc.). The distance to the service location can include a first distance from the technician's current location to a first location to obtain a specialized to and/or replacement part and a second distance from the first location to the service location.

At block 912, the technician selector 234 checks the clinical workflow corresponding to the machine. The clinical workflow corresponds to series of machines that are utilized to accomplish a particular task. Other machines in the clinical workflow can be evaluated to determine whether additional machines are to be serviced (e.g., are due for a checkup, are part of the issue, etc.) and/or whether the problem stems from another machine, for example. For example, when the output of a first machine is used in a second machine, where the problem was identified, then the problem can be cause be an invalid input. In such an example, even though the problem was identified in the second machine, the actual problem can be from the first machine. Accordingly, it can be desirable to select a technician that can service multiple machines or multiple technicians to service multiple machines in a clinical workflow to avoid sending out different technicians at different times.

At block 914, the technician selector 234 determines whether additional machines at the site location need to be serviced (e.g., other machines in the building or based on the clinical workflow are due for a checkup or also correspond to errors/issues). When the technician selector 234 determines that there are no additional machines at the site location that need to be serviced (block 914: NO), then the process continues to block 918. When the technician selector 234 determines that there are additional machines at the site location that need to be serviced (block 914: YES), then the weight multiple 236 adjusts preset weights of the available technicians based on the number of additional machines that the technician can service (block 916). For example, when the technician selector 234 identifies three machines that need to/should be serviced, then a higher weight is applied to technicians that can service all three and a lower weight is applied to technicians that can only service one. When a technician cannot service any of the machines, then a weight of zero is applied, thereby filtering out the technician unless they are the only technician available.

At block 918, the weight multiplier 236 adjusts the weights of the available technicians based on skill level, tools, distance, availability, etc. In some examples, the weight multiplier may utilize a neural network (e.g., the example neural network 500 of FIG. 5) to generate weights based on inputs including the skill level, tools, distance, etc. of the resources. The number of adjustments and/or the strength of the weights can be based on user/manufacture/customer preferences. For example, when time is a high priority for a customer, then distance and availability can receive higher weights than skill level. At block 920, the technician selector 234 determines the number of technicians needed to service the machines(s) at the side location. The number of technicians can be based on a contract with the customer, the availability of technicians, the complexity of the machine issue(s), and/or number of machines that need to be serviced. At block 922, the technician selector 234 selects the X highest weighted technicians, where X corresponds to the determined number of block 920. At block 924, the technician selector 234 transmits an indication of the service request with the corresponding care package to the selected technicians via the device interface 212.

Figure 10:
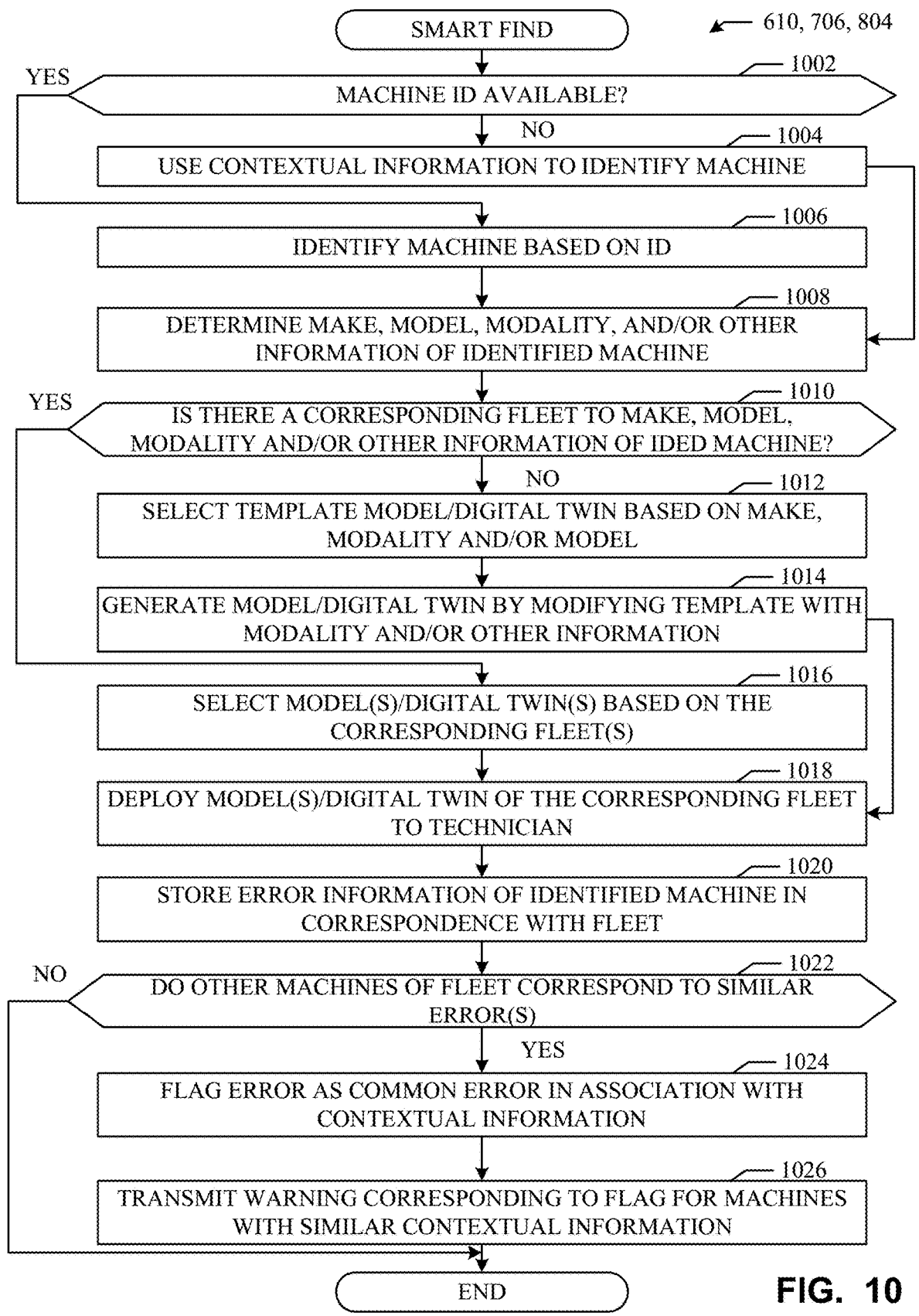
FIG. 10 is a flowchart representative of machine readable instructions which can be executed to implement the machine recovery system of FIGS. 1A and/or 1B to perform a smart find.

FIG. 10 includes a flowchart 610, 706, 802 representative of machine readable instructions that can be implemented by the structural components of the machine recovery system 102 of FIG. 2 to perform a smart find process. Although the flowchart 610, 706, 802 of FIG. 10 is described in conjunction with the machine recovery system 102 of FIGS. 1 and/or 2, other type(s) of recovery system(s) and/or other type(s) of processor(s) can be utilized instead.

At block 1002, the machine identifier 240 determines whether the machine ID is available. The machine ID can be provided by the user, the machine, the technician (e.g., when servicing the machine), and/or can be stored in conjunction with the machine 104 in one or more of the databases 216, 218, 220, 222. When the machine identifier 240 determines that the machine ID is not available (block 1002: NO), then the machine identifier 240 uses the machine identifier 240 can use obtained information about the machine 104 and compare the obtained information (e.g., contextual information) to stored information in the enterprise system(s) database 216 to identify the machine (block 1004). In some examples, the obtained information may include one or more photo(s) of the machine 104. In such an example, the machine identifier 240 utilize image processing techniques to determine distinct features of the machine 104 and/or where the machine 104 is located and compare the processed photos and/or distinct features to reference data and/or reference location information to identify the machine 104. In some examples, the machine identifier 420 may utilize a neural network (e.g., the example neural network 500 of FIG. 5) to identify the machine based on contextual information.

If the machine identifier 240 determines that the machine ID is available (block 1002: YES), the machine identifier 240 identifies the machine 104 based on the machine ID (block 1006). At block 1008, the machine identifier 240 determines the make, model, modality, and/or other information of the identified machine. For example, the machine identifier 240 can access the enterprise system(s) database 216 via the database interface 214 to obtain information corresponding to the identified machine. At block 1010, the model generator 242 determines whether there is a corresponding fleet to the make, model, modality and/or other information of the identified machine. The fleets of machines have similar makes, models, modalities, and/or other information. Information from a machine in a fleet can be used to diagnosis, predict problems, and/or service other machines in the fleet. Additionally, the fleets correspond to an artificial intelligence model(s) (e.g., a model, a digital twin, and/or a neural network) that has been customized based on information obtained from the fleet. In some examples, a machine can correspond to multiple fleets. The fleet information can be stored in the enterprise system(s) database 216.

If the model generator 242 determines that there is not a corresponding fleet of machines that (block 1010: NO), then the model generator 242 selects a template artificial intelligence model (e.g., model/digital twin, neural network, etc.) based on the make, modality, and/or model (block 1012). At block 1014, the model generator 242 generates an artificial intelligence model (e.g., model/digital twin, neural network, etc.) for the machine 104 by modifying the template artificial intelligence model (e.g., model/digital twin, neural network, etc.) with modality and/or other available information corresponding to the machine. When the model generator 242 determines that there is a corresponding fleet of machines that (block 1010: YES), then the model generator 242 selects the artificial intelligence model(s) (e.g., model(s), digital twin(s), neural network(s), etc.) of the corresponding fleet(s) (block 1016). At block 1018, the model generator 242 deploys the artificial intelligence model(s) (e.g., model(s), digital twin(s), neural network(s), etc.) of the corresponding fleet(s) to the device 108 of the technician (e.g., which can be included in the smart package) via the device interface 212. The technician can utilize the artificial intelligence model(s) (e.g., model(s), digital twin(s), neural network(s), etc.) as a test machine prior to/during service of the machine 104.

At block 1020, the information updater 246 stores the error information (e.g., the error codes, identified issues, etc.) of the identified machine in correspondence with the fleet (e.g., in the enterprise system(s) database 216 via the database interface 214, etc.). Using the error information, the fleet can track the error(s)/issue(s) of machines within the fleet to develop further analysis and/or to predict future errors within the fleet. At block 1022, the information updater 246 determines whether the other machines in the fleet correspond to similar error(s)/issue(s). When the information updater 246 determines that the other machines in the fleet correspond to similar error(s)/issue(s), then the information updater 246 flags the error/issue as a common error in association with contextual information (e.g., when the error occurred, the number of performances before the error occurred, the amount of time between the last servicing and the error, the age of the machine, location information, etc.). At block 1026, the device interface 212 transmits a warning corresponding to the flag for machines with similar contextual information. For example, when the error occurred when the machine 104 was operational for five years, then the device interface 212 can transmit a warning to other machines that have been operation for more than four years. The device interface 212 can transmit the warning to the device, to a user of the device (e.g., via email, text message, etc.), to the customer, to the manager of the machine recovery system 102, to the service center 106, and/or to any other related party.

Figure 11:
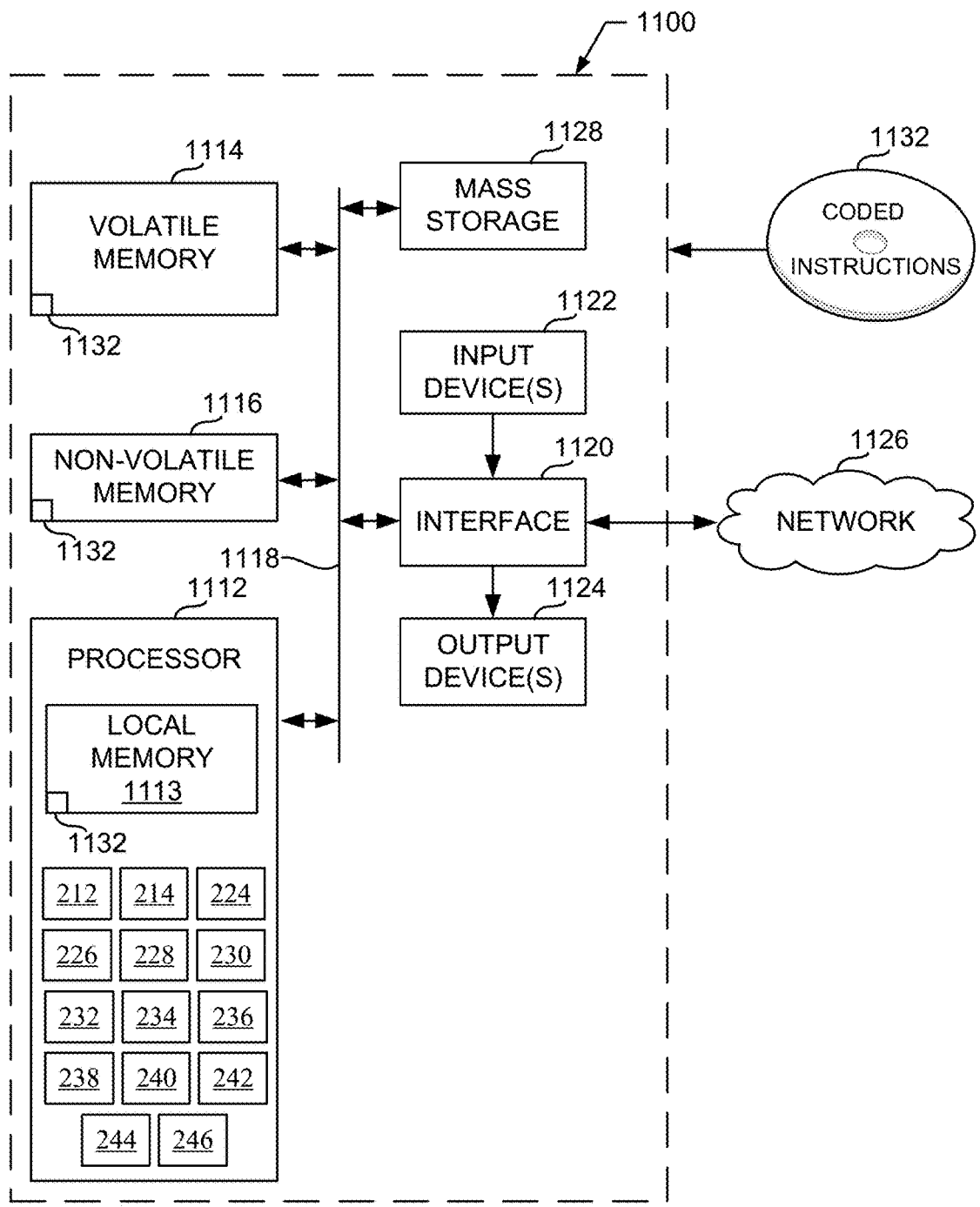
FIG. 11 is a block diagram of an example processing platform structured to execute the instructions of FIGS. 6-10 to implement the machine recovery system of FIGS. 1A and/or 1B.

FIG. 11 is a block diagram of a processor platform 1100 structured to execute the instructions of FIGS. 6, 7, 8, 9, and/or 10 to implement the machine recovery system 102 of FIG. 2. The processor platform 1100 can be, for example, a server, a personal computer, a workstation, a self-learning machine (e.g., a neural network), an Internet appliance, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors, GPUs, DSPs, or controllers from any desired family or manufacturer. The hardware processor can be a semiconductor based (e.g., silicon based) device. In this example, the processor 1112 implements the device interface 212, the database interface 214, the symptom processor 224, the filter 226, the care package generator 228, the solution predictor 230, the remote instruction executor 232, the technician selector 234, the weight multiplier 236, the technician database 238, the machine identifier 240, the model generator 242, the survey generator 244, the information updater 246, and the database interface 214.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 can be implemented by Synchronous Dynamic Random Access Memory (SDRAM), Dynamic Random Access Memory (DRAM), RAMBUS® Dynamic Random Access Memory (RDRAM®) and/or any other type of random access memory device. The non-volatile memory 1116 can be implemented by flash memory and/or any other desired type of memory device. Access to the main memory 1114, 1116 is controlled by a memory controller.

The processor platform 1100 of the illustrated example also includes an interface circuit 1120. The interface circuit 1120 can be implemented by any type of interface standard, such as an Ethernet interface, a universal serial bus (USB), a Bluetooth® interface, a near field communication (NFC) interface, and/or a PCI express interface.

In the illustrated example, one or more input devices 1122 are connected to the interface circuit 1120. The input device(s) 1122 permit(s) a user to enter data and/or commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer and/or speaker. The interface circuit 1120 of the illustrated example, thus, typically includes a graphics driver card, a graphics driver chip and/or a graphics driver processor.

The interface circuit 1120 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1126. The communication can be via, for example, an Ethernet connection, a tech subscriber line (DSL) connection, a telephone line connection, a coaxial cable system, a satellite system, a line-of-site wireless system, a cellular telephone system, etc.

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, redundant array of independent disks (RAID) systems, and digital versatile disk (DVD) drives.

The machine executable instructions 1132 of FIGS. 6, 7, 8, 9, and/or 10 can be stored in the mass storage device 1128, in the volatile memory 1114, in the non-volatile memory 1116, and/or on a removable non-transitory computer readable storage medium such as a CD or DVD.

From the foregoing, it will be appreciated that example methods, apparatus and articles of manufacture have been disclosed that provide new, technologically advanced imaging modality maintenance, monitoring, and repair. The disclosed methods, apparatus and articles of manufacture improve the efficiency of using a computing device by transforming the computing device into a diagnostic and repair tool to receive symptom and/or configuration information (e.g., through data transfer, measurement, monitoring, etc.) for a machine, identify a problem for that machine and/other connected component(s), model and drive selection of a solution to the problem, and identify appropriate resource(s) to execute the solution to ameliorate the symptom(s)/problem(s) at a machine. Certain examples provide simulation through modeling and/or network analysis and generate a care package to be deployed to fix a problem. The disclosed methods, apparatus and articles of manufacture are accordingly directed to one or more improvement(s) in the functioning of a computer.

For example, outcomes and observed behavior can be modeled to develop realistic, physics-based virtual counterparts to imaging modality devices, repair resources, environments, etc., and/or robust learning network models to generate solutions from indications of a problem for a machine. Certain examples factor in a severity of a problem, an immediacy of a problem, a scope of a problem, as well as available tools, technicians, and/or other resources to generate a packaged solution to address the issue for the target machine and/or other machines in its fleet, other devices in its environment, other components on its care path/protocol, etc. Rather than sending inadequate resources enable to solve an issue, spend hundreds of dollars a day on travel and time, allow issues to intensify and cost more to fix, resulting in greater machine unavailability, certain examples generate a repair or care package to diagnose and/or treat issue(s) with machine(s). Solutions can be tailored to a particular machine in a particular environment and/or can extend to similar machines at a location, in a fleet, etc. While prior approaches involved manual technician investigation, certain examples provide customized, evolving solutions for particular machine(s) with particular problem(s). For example, an MR machine used for 12 scan a day can be modeled and treated differently than another MR machine used for 30 scans a day. Machines can be compared to allocate a same response and/or deviate to develop a different response for a machine whose usage pattern is different from others in the fleet. Certain examples provide fleet modeling, site modeling, workflow/protocol modeling, etc., to leverage environment for the benefit of machine repair and leverage one machine's repair for the benefit of the larger environment.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A non-transitory computer readable storage medium comprising instructions which, when executed, cause a machine to at least:
   model a problem using an artificial intelligence model of an imaging device based on information obtained from a service request from the imaging device;
   identify at least one of a skill level, tools list, or replacement part list to fix the problem based on the modeling using the artificial intelligence model;
   access resources from a database of resources available to service the imaging device to identify a set of one or more available resources;
   in response to the service request for the imaging device corresponding to an issue, determine whether the issue of the imaging device corresponds to a critical error;
   when the issue of the imaging device corresponds to the critical error, filter out resources that are not available to service the imaging device within a threshold amount of time to reduce the set of one or more available resources;
   weight resources in the set of one or more available resources based on at least one of the skill level, possessed tools in comparison to the tools list, possessed replacement parts in comparison to the replacement part list, distance to service location, or availability to identify a highest weighted resource; and
   transmit the service request using a wireless communication to a repair device associated with the highest weighed resource.

2. The computer readable storage medium of claim 1, wherein the critical error is defined by at least one of a manufacturer of the imaging device or a customer.

3. The computer readable storage medium of claim 1, wherein the instructions cause the machine to determine if the resource is available to service the imaging device based on at least one of an availability of the resource or a distance of the resource to the service location.

4. The computer readable storage medium of claim 3, wherein the distance of the resource to the service location includes a first distance from a first location of the resource to a second location of at least one of a tool or a replacement needed for the service request and a second distance from the second location to the service location.

5. The computer readable storage medium of claim 1, wherein the instructions cause the machine to determine a clinical workflow corresponding to the imaging device.

6. The computer readable storage medium of claim 5, wherein the instructions cause the machine to identify additional imaging devices for servicing based on the clinical workflow.

7. The computer readable storage medium of claim 6, wherein the instructions cause the machine to weight the resources based on a number of the additional imaging devices that a technician is capable of servicing.

8. The computer readable storage medium of claim 1, wherein the artificial intelligence model is at least one of a digital twin of the imaging device or a neural network.

9. The computer readable storage medium of claim 1, wherein the service request is included in a care package.

10. An apparatus comprising:
a technician selector to:
identify at least one of a skill level, tools list, or replacement part list to fix a problem based on an identified problem corresponding to a service request from an imaging device; and
access resources from a database of resources available to service the imaging device;
a multiplier to weight resources based on at least one of the skill level, possessed tools in comparison to the tools list, possessed replacement parts in comparison to the replacement part list, distance to a location of the imaging device, or availability; and
an interface to transmit the service request using a wireless communication to a repair device of the highest weighed resource, the service request to be augmented to include a configuration for the repair device to facilitate addressing of the service request by the highest weighted resource.

11. The apparatus of claim 10, wherein the technician selector is to, when the identified problem corresponds to a critical error, remove resources that are not available within a threshold amount of time, the critical error defined by at least one of a manufacturer of the imaging device or a customer.

12. The apparatus of claim 10, wherein the technician selector is to determine if the resource is available to service the imaging device based on at least one of an availability of the resource or a distance of the resource to the location of the imaging device.

13. The apparatus of claim 12, wherein the distance of the resource to the location of the imaging device includes a first distance from a first location of the resource to a second location of at least one of a tool or a replacement needed for the service request and a second distance from the second location to the location of the imaging device.

14. The apparatus of claim 10, wherein the technician selector is to determine a clinical workflow corresponding to the imaging device.

15. The apparatus of claim 14, wherein the technician selector is to identify additional imaging devices for servicing based on the clinical workflow.

16. The apparatus of claim 15, wherein the multiplier is to weight the resources based on a number of the additional imaging devices that a technician is capable of servicing.

17. The apparatus of claim 10, wherein the service request is included in a care package.

18. A method comprising:
identifying, by executing an instruction with a processor, at least one of a skill level, tools list, or replacement part list to fix a problem of a machine based on a digital twin of the machine;
accessing resources from a database of resources available to service an imaging device;
determining, by executing an instruction with the processor, whether the problem of the imaging device corresponds to a critical error;
when the problem of the imaging device corresponds to the critical error, removing, by executing an instruction with the processor, resources who are not available to service the imaging device within a threshold amount of time;
weighting, by executing an instruction with the processor, resources based on at least one of the skill level, possessed tools in comparison to the tools list, possessed replacement parts in comparison to the replacement part list, distance to service location, or availability to determine a highest weighted resource; and
transmitting a service request corresponding to the imaging device to a repair device of the highest weighed resource using a wireless communication.

19. The method of claim 18, wherein the critical error defined by at least one of a manufacturer of the imaging device or a customer.

20. The method of claim 18, further including determining if a technician is available to service the imaging device based on at least one of an availability of the resource or a distance of the resource to the location of the imaging device.

* * * * *